US012333722B1

(12) United States Patent
Dresser et al.

(10) Patent No.: US 12,333,722 B1
(45) Date of Patent: Jun. 17, 2025

(54) SYSTEMS AND METHODS FOR PREDICTING MEDICAL CONDITIONS USINGMACHINE LEARNING CORRELATING DENTAL IMAGES AND MEDICAL DATA

(71) Applicant: Enamel Pure, Inc., Worcester, MA (US)

(72) Inventors: Charles Holland Dresser, Wayland, MA (US); Nathan Paul Monty, Shrewsbury, MA (US)

( * ) Notice: Subject to any disclaimer, the term of this patent is extended or adjusted under 35 U.S.C. 154(b) by 0 days.

(21) Appl. No.: 18/619,331

(22) Filed: Mar. 28, 2024

(51) Int. Cl.
| | |
|---|---|
| *G06T 7/00* | (2017.01) |
| *G16H 10/60* | (2018.01) |
| *G16H 30/40* | (2018.01) |
| *G16H 50/20* | (2018.01) |

(52) U.S. Cl.
CPC ........... *G06T 7/0012* (2013.01); *G16H 10/60* (2018.01); *G16H 30/40* (2018.01); *G16H 50/20* (2018.01); *G06T 2207/20084* (2013.01); *G06T 2207/30036* (2013.01)

(58) Field of Classification Search
CPC ......... G06T 7/0012; G06T 2207/20084; G06T 2207/30036; G16H 10/60; G16H 30/40; G16H 50/20
See application file for complete search history.

(56) References Cited

U.S. PATENT DOCUMENTS

| | | | |
|---|---|---|---|
| 5,055,048 A | 10/1991 | Vassiliadis et al. | |
| 5,275,564 A | 1/1994 | Vassiliadis et al. | |
| 7,013,191 B2 | 3/2006 | Rubbert et al. | |
| 7,090,497 B1 | 8/2006 | Harris et al. | |
| 9,463,081 B2 | 10/2016 | Urakabe et al. | |
| 9,864,485 B2 | 1/2018 | Patton et al. | |
| 10,219,685 B2 | 3/2019 | Hakomori et al. | |
| 10,390,913 B2 | 8/2019 | Sabina et al. | |
| 10,506,929 B2 | 12/2019 | Almoumen et al. | |
| 10,509,838 B2 | 12/2019 | Elbaz et al. | |
| 10,850,115 B2 | 12/2020 | Zhou et al. | |
| 11,357,404 B2 | 6/2022 | Atiya et al. | |
| 11,357,603 B2 | 6/2022 | Elbaz et al. | |
| 11,478,314 B1 | 10/2022 | Roh et al. | |

(Continued)

FOREIGN PATENT DOCUMENTS

| | | |
|---|---|---|
| AU | 2004223469 B2 | 7/2009 |
| AU | 2012206109 B2 | 2/2015 |

(Continued)

*Primary Examiner* — Van D Huynh

(57) ABSTRACT

Embodiments of the present disclosure may include a system for associating dental and medical data the system including a processor. Embodiments may also include a memory containing instructions that instruct the processor to receive dental data including a plurality of dental images representative of at least a surface of dental tissue of a patient. Embodiments may also include receive medical data representative of the patient. Embodiments may also include generate training data as a function of a correlation between the dental data and the medical data. Embodiments may also include input the training data into a machine learning algorithm. Embodiments may also include train a machine learning model as a function of the training data and the machine learning algorithm.

20 Claims, 15 Drawing Sheets

(56) References Cited

U.S. PATENT DOCUMENTS

| | | | |
|---|---|---|---|
| 11,948,685 B2* | 4/2024 | Ricci | G16H 70/20 |
| 2003/0158544 A1 | 8/2003 | Slatkine et al. | |
| 2005/0259933 A1 | 11/2005 | Temelkuran et al. | |
| 2007/0134615 A1 | 6/2007 | Lovely et al. | |
| 2010/0009308 A1 | 1/2010 | Wen et al. | |
| 2014/0272764 A1 | 9/2014 | Miller et al. | |
| 2016/0012182 A1 | 1/2016 | Golay et al. | |
| 2016/0113495 A1 | 4/2016 | Nanuundappa et al. | |
| 2016/0135925 A1 | 5/2016 | Mason et al. | |
| 2016/0143703 A1 | 5/2016 | Monty et al. | |
| 2016/0154468 A1 | 6/2016 | Kimmel et al. | |
| 2017/0215989 A1 | 8/2017 | Gregg et al. | |
| 2017/0308981 A1* | 10/2017 | Razavian | G16H 40/60 |
| 2018/0028065 A1 | 2/2018 | Elbaz et al. | |
| 2018/0085002 A1 | 3/2018 | Glinec et al. | |
| 2018/0356501 A1 | 12/2018 | Send et al. | |
| 2018/0357766 A1* | 12/2018 | Van Der Poel | A61B 5/4547 |
| 2019/0125250 A1 | 5/2019 | Monty et al. | |
| 2019/0192262 A1 | 6/2019 | Pesach et al. | |
| 2019/0247050 A1 | 8/2019 | Goldsmith et al. | |
| 2019/0313963 A1* | 10/2019 | Hillen | G06V 10/764 |
| 2019/0328489 A1 | 10/2019 | Capron Richard et al. | |
| 2020/0066391 A1 | 2/2020 | Sachdeva et al. | |
| 2020/0146646 A1* | 5/2020 | Tuzoff | G06T 7/11 |
| 2020/0214538 A1 | 7/2020 | Pesach et al. | |
| 2020/0306011 A1 | 10/2020 | Chekhonin et al. | |
| 2020/0315754 A1 | 10/2020 | Ciriello et al. | |
| 2020/0405242 A1* | 12/2020 | Kearney | G06N 3/088 |
| 2021/0073977 A1* | 3/2021 | Carter | G06T 11/20 |
| 2021/0074061 A1* | 3/2021 | Brown | G16H 30/40 |
| 2021/0125732 A1* | 4/2021 | Patel | G06N 5/01 |
| 2021/0134440 A1* | 5/2021 | Menavsky | G16H 40/20 |
| 2021/0137653 A1 | 5/2021 | Saphier et al. | |
| 2021/0145538 A1 | 5/2021 | Boutoussov et al. | |
| 2021/0321872 A1 | 10/2021 | Saphier et al. | |
| 2021/0353216 A1 | 11/2021 | Hillen et al. | |
| 2022/0023003 A1 | 1/2022 | Cramer et al. | |
| 2022/0249214 A1 | 8/2022 | Serval et al. | |
| 2023/0298176 A1* | 9/2023 | Choi | G06N 7/01 703/11 |

FOREIGN PATENT DOCUMENTS

| | | | |
|---|---|---|---|
| BR | 112021014639 | A2 | 9/2021 |
| CN | 105358092 | A | 2/2016 |
| CN | 107529968 | A | 1/2018 |
| CN | 111083922 | A | 4/2020 |
| CN | 211381887 | U | 9/2020 |
| CN | 114302672 | A | 4/2022 |
| EP | 2569748 | A1 | 3/2013 |
| EP | 2204136 | B1 | 8/2013 |
| EP | 3684292 | A4 | 6/2021 |
| ES | 2758839 | T3 | 5/2020 |
| JP | 6018618 | B2 | 11/2016 |
| JP | 6262936 | B2 | 1/2018 |
| JP | 6673703 | B2 | 3/2020 |
| KR | 101277226 | B1 | 6/2013 |
| KR | 101483216 | B1 | 1/2015 |
| PH | 11999002531 | B | 3/2002 |
| WO | 0009030 | A1 | 2/2000 |
| WO | 0019929 | A1 | 4/2000 |
| WO | 2018112273 | A2 | 6/2018 |
| WO | 2019023631 | A1 | 1/2019 |
| WO | 2019093426 | A1 | 5/2019 |
| WO | 2019207588 | A2 | 10/2019 |
| WO | 2021155054 | A1 | 8/2021 |
| WO | 2022020267 | A1 | 1/2022 |
| WO | 2022119930 | A1 | 6/2022 |
| WO | 2022212507 | A1 | 10/2022 |

\* cited by examiner

SYSTEMS AND METHODS FOR PREDICTING MEDICAL CONDITIONS USINGMACHINE LEARNING CORRELATING DENTAL IMAGES AND MEDICAL DATA

FIELD OF THE DISCLOSURE

The present invention relates to systems and methods for predicting medical conditions using dental data and machine learning. More specifically, aspects of the invention involve receiving dental images, pre-processing the images using techniques such as 3D reconstruction, and inputting the processed data into a pre-trained machine learning model to predict a patient's medical condition based on correlations between dental images and medical data.

BACKGROUND OF THE INVENTION

In recent years, there has been a growing interest in exploring the relationship between oral health and overall health. Numerous studies have suggested that dental conditions, such as periodontal disease, can be associated with various systemic health issues, including cardiovascular disease, diabetes, and respiratory disorders. However, the complex interactions between oral health and general health are not yet fully understood.

SUMMARY

There is a need for more advanced methods to identify and predict potential medical conditions based on dental data. It is therefore an object of the current invention to address these challenges and opportunities by developing a comprehensive system and method for predicting medical conditions using dental data and advanced machine learning techniques. By leveraging state-of-the-art data acquisition technologies and innovative algorithms, this invention aims to provide a powerful tool for early detection and personalized management of potential health risks, ultimately improving patient care and outcomes.

The following summary provides an overview of some of the key inventive features of the systems and methods for predicting medical conditions using dental data and machine learning. This summary is not an extensive overview of the invention and is not intended to identify all key or critical elements of the invention or to delineate the scope of the invention. Its sole purpose is to present some concepts of the invention in a simplified form as a prelude to the more detailed description that is presented later.

Advances in dental data acquisition technologies have made it possible to collect a wealth of information about a patient's oral health. Digital imaging techniques, such as intraoral scanners and cone-beam computed tomography (CBCT), can provide detailed 2D and 3D representations of dental tissues, including teeth, gums, and supporting structures. These imaging modalities offer high-resolution data that can be used for diagnostic and treatment planning purposes. Additionally, electronic dental records (EDRs) have become increasingly prevalent, allowing for the storage and sharing of comprehensive patient data, including medical histories, treatment plans, and outcomes.

Concurrent with the growth in dental data acquisition capabilities, the field of machine learning has experienced significant advancements. Machine learning algorithms, particularly deep learning neural networks, have demonstrated remarkable performance in tasks such as image recognition, natural language processing, and predictive modeling. These algorithms can learn complex patterns and relationships from large datasets, making them well-suited for analyzing the vast amounts of dental data available.

The convergence of advanced dental data acquisition technologies and machine learning techniques presents a unique opportunity to develop innovative approaches for predicting medical conditions based on dental data. By leveraging the rich information contained within dental images and records, machine learning models can potentially uncover hidden correlations and patterns that may indicate the presence or risk of certain medical conditions. This could enable earlier detection, intervention, and personalized treatment strategies, ultimately improving patient outcomes and quality of life.

Despite the potential benefits, there are challenges to be addressed in developing such predictive models. These include ensuring the quality and standardization of dental data, integrating data from multiple sources, and validating the accuracy and generalizability of the models. Additionally, there are ethical considerations surrounding the use of patient data and the potential impact on privacy and informed consent.

One aspect of the present disclosure relates to a system for associating dental and medical data. The system may include one or more hardware processors configured by machine-readable instructions for associating dental and medical data. The machine-readable instructions may be configured to receive, using a computing device, dental data comprising a plurality of dental images representative of at least a surface of dental tissue of a patient. The machine-readable instructions may be configured to receive, using the computing device, medical data representative of the patient. The machine-readable instructions may be configured to generate, using the computing device, training data as a function of a correlation between the dental data and the medical data. The machine-readable instructions may be configured to input, using the computing device, the training data into a machine learning algorithm. The machine-readable instructions may be configured to train, use the computing device, a machine learning model as a function of the training data and the machine learning algorithm.

Another aspect of the present disclosure relates to a method for associating dental and medical data. The method may include receiving, using a computing device, dental data comprising a plurality of dental images representative of at least a surface of dental tissue of a patient. The method may include receiving, using the computing device, medical data representative of the patient. The method may include generating, using the computing device, training data as a function of a correlation between the dental data and the medical data. The method may include inputting, using the computing device, the training data into a machine learning algorithm. The method may include training, using the computing device, a machine learning model as a function of the training data and the machine learning algorithm.

BRIEF DESCRIPTION OF THE DRAWING

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION OF THE INVENTION

As used herein, the terms "comprising," "including," "containing," "characterized by," and grammatical equivalents thereof are inclusive or open-ended and do not exclude additional, unrecited elements or method steps, unless otherwise stated. Other than in the operating examples, or where otherwise indicated, all numbers expressing measurements, dimensions, and so forth used in the specification and claims are to be understood as being modified in all instances by the term "about," meaning within a reasonable range of the indicated value.

The present invention provides novel systems and methods for associating dental and medical data, as well as predicting medical conditions using dental data and machine learning techniques. The invention comprises specific structural elements, such as processors, memory, and machine-readable instructions, arranged in a defined configuration and designed to address the limitations of existing methods for integrating dental and medical data. The following detailed description discloses various embodiments, aspects, and features of the present invention, which are not intended to limit the scope of the invention in any way but rather to exemplify the preferred embodiments. These embodiments include systems and methods for receiving dental images and medical data, generating training data based on correlations between the dental and medical data, training machine learning models using the training data, and predicting medical conditions based on the trained models and input dental data. The invention also encompasses various pre-processing techniques, such as 3D reconstruction of dental images, to enhance the predictive capabilities of the machine learning models.

Figure 1:
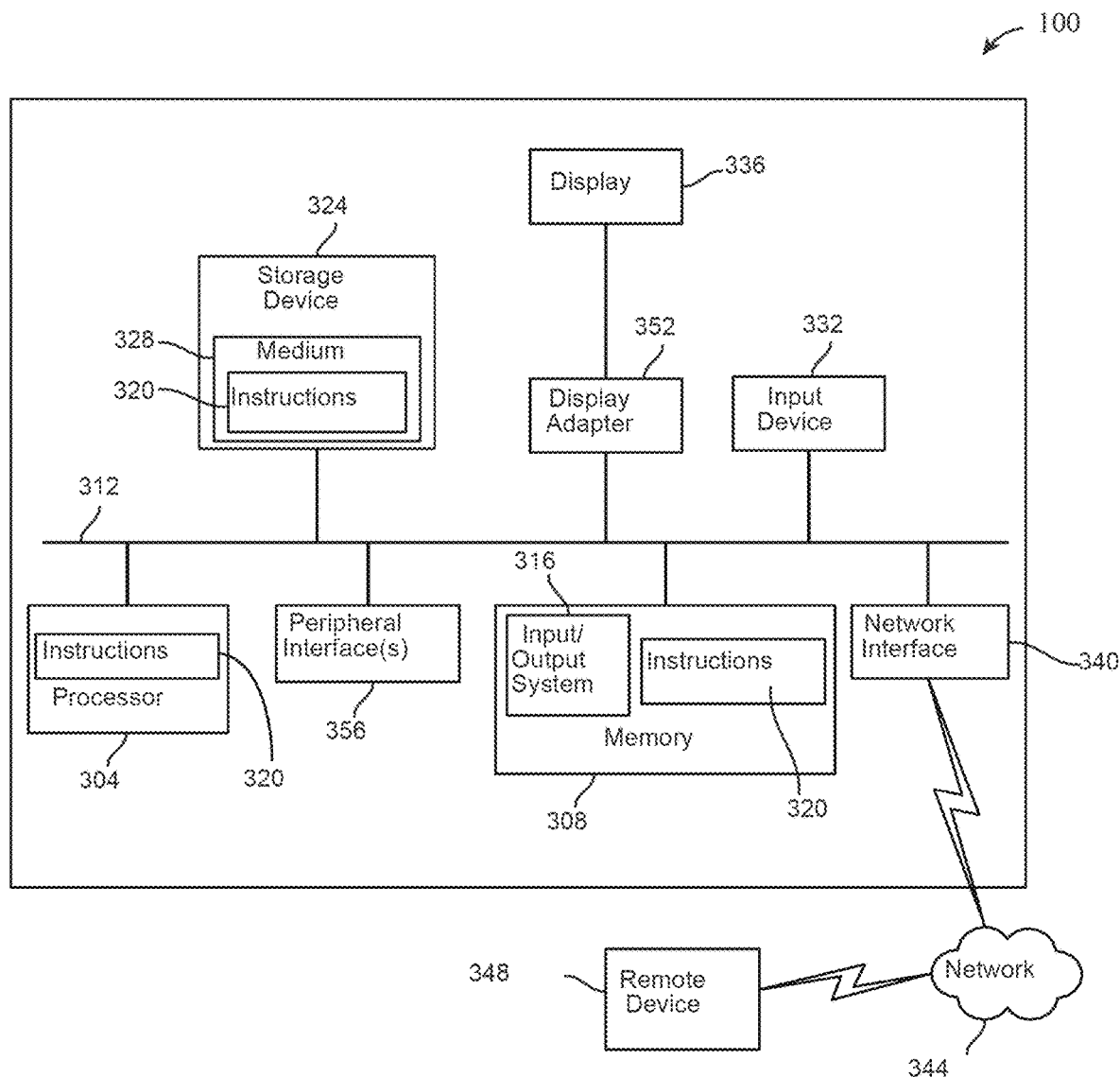
FIG. 1 is a system for associating dental and medical data, including a processor, memory, input device, user input device, and output device.

Referring now to FIG. 1, an exemplary embodiment of a system for associating dental and medical data and predicting medical conditions using dental data is illustrated. The system includes a computing device, which comprises a processor communicatively connected to a memory. As used in this disclosure, "communicatively connected" means connected by way of a connection, attachment or linkage between two or more components which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, dental images, medical data, training data, machine learning models, and the like. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1, the computing device may include any computing device as described in this disclosure, including without limitation a microcontroller, microprocessor, digital signal processor (DSP) and/or system on a chip (SoC). The computing device may include, be included in, and/or communicate with a mobile device such as a mobile telephone or smartphone. The computing device may include a single computing device operating independently, or may include two or more computing devices operating in concert, in parallel, sequentially or the like; two or more computing devices may be included together in a single computing device or in two or more computing devices. The computing device may interface or communicate with one or more additional devices, such as dental imaging systems, electronic health record databases, or medical diagnostic equipment, via a network interface device. The network interface device may be utilized for connecting the computing device to one or more of a variety of networks, enabling communication with other devices and systems involved in dental and medical data integration. Examples of a network include, but are not limited to, a wide area network (e.g., the Internet, an enterprise network), a local area network (e.g., a network associated with a dental practice, a hospital, or other healthcare facility), a data network associated with a healthcare provider, a direct connection between two computing devices, and any combinations thereof. A network may employ a wired and/or a wireless mode of communication. In general, any network topology may be used. Information (e.g., dental images, medical data, training data, machine learning models) may be communicated to and/or from the computing device. The computing device may include but is not limited to, for example, a computing device or cluster of computing devices in a dental practice and a second computing device or cluster of computing devices in a medical facility. The computing device may include one or more computing devices dedicated to data storage, security, distribution of traffic for load balancing, and the like. The computing device may distribute one or more computing tasks, such as pre-processing dental images, generating training data, or training machine learning models, across a plurality of computing devices, which may operate in parallel, in series, redundantly, or in any other manner used for distribution of tasks or memory between computing devices. The computing device may be implemented, as a non-limiting example, using a "shared nothing" architecture.

With continued reference to FIG. 1, the computing device may be designed and/or configured to perform any method, method step, or sequence of method steps in any embodiment described in this disclosure, in any order and with any degree of repetition. For instance, the computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. The computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. For example, the computing device may iteratively pre-process dental images using different techniques or parameters, aggregate the results, and use them as inputs for generating training data. Similarly, the computing device may train multiple machine learning models in parallel, each focusing on different aspects of the dental-medical data correlation, and combine their outputs to produce a comprehensive prediction of medical conditions. The computing device may also recursively refine its predictions by using the outputs of one iteration of the machine learning model as inputs for the next iteration, gradually improving the accuracy and reliability of the results. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing in the context of associating dental and medical data and predicting medical conditions using dental data and machine learning techniques.

It is to be noted that any one or more of the aspects and embodiments described herein may be conveniently implemented using one or more machines (e.g., one or more computing devices that are utilized as a user computing device for dental and medical data processing, one or more server devices, such as a data server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein. This may include data related to dental images, medical records, training data for machine learning models, and predictions of medical conditions based on dental data.

Examples of a computing device include, but are not limited to, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In the context of this invention, a computing device may be used to process dental images, medical records, and other data to train machine learning models and predict medical conditions based on dental data. These computing devices may be located in dental practices, hospitals, research institutions, or other healthcare facilities, and may communicate with each other via local or wide area networks to facilitate the integration and analysis of dental and medical data.

FIG. 1 shows a diagrammatic representation of one embodiment of a computing device in the exemplary form of a computer system 100 within which a set of instructions for causing the system to perform any one or more of the aspects and/or methodologies of the present disclosure related to associating dental and medical data and predicting medical conditions using dental data may be executed. It is also contemplated that multiple computing devices may be utilized to implement a specially configured set of instructions for causing one or more of the devices to perform any one or more of the aspects and/or methodologies of the present disclosure. Computer system 300 includes a processor 304 and a memory 308 that communicate with each other, and with other components, via a bus 312. Bus 312 may include any of several types of bus structures including, but not limited to, a memory bus, a memory controller, a peripheral bus, a local bus, and any combinations thereof, using any of a variety of bus architectures.

Processor 304 may include any suitable processor for executing instructions related to receiving dental images and medical data, generating training data, training machine learning models, and predicting medical conditions based on dental data. This may include, without limitation, a processor incorporating logical circuitry for performing arithmetic and logical operations, such as an arithmetic and logic unit (ALU), which may be regulated with a state machine and directed by operational inputs from memory and/or sensors; processor 304 may be organized according to Von Neumann and/or Harvard architecture as a non-limiting example. Processor 304 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 308 may include various components (e.g., machine-readable media) including, but not limited to, a random-access memory component, a read only component, and any combinations thereof. In one example, a basic input/output system 316 (BIOS), including basic routines that help to transfer information between elements within computer system 300, such as during start-up, may be stored in memory 308. Memory 308 may also include (e.g., stored on one or more machine-readable media) instructions (e.g., software) 320 embodying any one or more of the aspects and/or methodologies of the present disclosure, such as instructions for pre-processing dental images, generating training data, training machine learning models, and predicting medical conditions based on dental data. In another example, memory 308 may further include any number of program modules including, but not limited to, an operating system, one or more application programs specific to dental and medical data integration and analysis, other program modules, program data such as dental images, medical records, and machine learning models, and any combinations thereof.

Computer system 100 may also include a storage device 324. Examples of a storage device (e.g., storage device 324) include, but are not limited to, a hard disk drive, a magnetic disk drive, an optical disc drive in combination with an optical medium, a solid-state memory device, and any combinations thereof. Storage device 324 may be connected to bus 312 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 324 (or one or more components thereof) may be removably interfaced with computer system 100 (e.g., via an external port connector (not shown)). Particularly, storage device 324 and an associated machine-readable medium 328 may provide nonvolatile and/or volatile storage of machine-readable instructions, data structures, program modules, and/or other data for computer system 100. In one example, software 320 may reside, completely or partially, within machine-readable medium 328. In another example, software 320 may reside, completely or partially, within processor 304.

Computer system 100 may also include an input device 332. In one example, a user of computer system 100 may enter commands and/or other information into computer system 100 via input device 332. Examples of an input device 332 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 332 may be interfaced to bus 312 via any of a variety of interfaces (not shown) including, but not limited to, a serial interface, a parallel interface, a game port, a USB interface, a FIRE-WIRE interface, a direct interface to bus 312, and any combinations thereof. Input device 332 may include a touch screen interface that may be a part of or separate from display 336, discussed further below. Input device 332 may be utilized as a user selection device for selecting one or more graphical representations in a graphical interface as described above.

A user may also input commands and/or other information to computer system 100 via storage device 324 (e.g., a removable disk drive, a flash drive, etc.) and/or network interface device 340. A network interface device, such as network interface device 340, may be utilized for connecting computer system 100 to one or more of a variety of networks, such as network 344, and one or more remote devices 348 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 344, may employ a wired and/or a wireless mode of communication. In general, any network topology may be used. Information (e.g., data, software 320, etc.) may be communicated to and/or from computer system 100 via network interface device 340.

Computer system 100 may further include a video display adapter 352 for communicating a displayable image to a display device, such as display device 336. Examples of a display device include, but are not limited to, a liquid crystal display (LCD), a cathode ray tube (CRT), a plasma display, a light emitting diode (LED) display, and any combinations thereof. Display adapter 352 and display device 336 may be utilized in combination with processor 304 to provide graphical representations of aspects of the present disclosure, such as visualizations of dental images, medical data, machine learning model outputs, and predicted medical conditions. In addition to a display device, computer system 100 may include one or more other peripheral output devices including, but not limited to, an audio speaker, a printer, and any combinations thereof. Such peripheral output devices may be connected to bus 312 via a peripheral interface 356. Examples of a peripheral interface include, but are not limited to, a serial port, a USB connection, a FIREWIRE connection, a parallel connection, and any combinations thereof. These peripheral devices may be used to provide alerts, notifications, or hard copies of results related to the prediction of medical conditions based on dental data.

Still referring to FIG. 1, in some embodiments, the system 100 for associating dental and medical data may additionally include at least a camera. As used in this disclosure, a "camera" is a device that is configured to sense electromagnetic radiation, such as without limitation visible light, and generate an image representing the electromagnetic radiation. In the context of dental imaging, cameras may be used to capture detailed visual information of a patient's oral cavity, including teeth, gums, and other dental structures.

In some cases, a dental camera may include one or more optics. Exemplary non-limiting optics include spherical lenses, aspherical lenses, reflectors, polarizers, filters, windows, aperture stops, and the like. These optical components help to focus, direct, and manipulate the light entering the camera, enabling the capture of high-quality dental images. In some cases, at least a dental camera may include an image sensor. Exemplary non-limiting image sensors include digital image sensors, such as without limitation charge-coupled device (CCD) sensors and complementary metal-oxide-semiconductor (CMOS) sensors, chemical image sensors, and analog image sensors, such as without limitation film. These image sensors convert the light captured by the camera into an electronic or chemical signal that can be processed to form a digital or analog dental image.

In some cases, a dental camera may be sensitive within a non-visible range of electromagnetic radiation, such as without limitation infrared. This can be particularly useful for detecting dental issues that may not be apparent in the visible spectrum, such as early stages of tooth decay or inflammation in the gums.

As used in this disclosure, "image data" is information representing at least a physical scene, space, and/or object. In the context of dental imaging, image data represents the visual information captured by the dental camera, depicting the patient's oral cavity and dental structures. In some cases, dental image data may be generated by a camera. "Image data" may be used interchangeably throughout this disclosure with "image," where image is used as a noun. A dental image may be optical, such as without limitation when at least an optic is used to generate an image of a dental object. A dental image may be material, such as without limitation when film is used to capture a dental image. A dental image may be digital, such as without limitation when represented as a bitmap. Alternatively, a dental image may be comprised of any media capable of representing a physical scene, space, and/or object within the oral cavity.

Alternatively, where "image" is used as a verb in this disclosure, it refers to the generation and/or formation of a dental image. In the context of the system for associating dental and medical data, the process of imaging involves using a dental camera to capture visual information of the patient's oral cavity, which can then be processed and analyzed to predict medical conditions or identify correlations between dental and systemic health.

Still referring to FIG. 1, in some embodiments, the system 100 for associating dental and medical data may include a machine vision system that includes at least a camera. A machine vision system may use images from at least a camera to make a determination about a scene, space, and/or object within the oral cavity. In the context of dental imaging, a machine vision system can be employed to analyze and interpret the captured dental images, enabling the identification of specific dental features, structures, and potential abnormalities.

In some cases, the machine vision system may be used for world modeling or registration of objects within the oral cavity. Registration may include image processing techniques, such as without limitation object recognition, feature detection, edge/corner detection, and the like. Non-limiting examples of feature detection may include scale invariant feature transform (SIFT), Canny edge detection, Shi Tomasi corner detection, and the like. These techniques allow the machine vision system to identify and locate specific dental structures, such as teeth, gums, and other anatomical landmarks, within the captured dental images.

In some cases, registration may include one or more transformations to orient a dental camera frame (or a dental image or video stream) relative to a three-dimensional coordinate system of the oral cavity. Exemplary transformations include without limitation homography transforms and affine transforms. These transformations enable the machine vision system to map the 2D dental images onto a 3D representation of the oral cavity, providing a more comprehensive and accurate understanding of the spatial relationships between dental structures.

In an embodiment, registration of the first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame. However, a third dimension of registration, representing depth and/or a z-axis, may be detected by comparison of two frames. For instance, where the first frame includes a pair of frames captured using a pair of cameras (e.g., stereoscopic camera, also referred to in this disclosure as a stereo-camera), image recognition and/or edge detection software may be used to detect a pair of stereoscopic views of images of a dental object. The two stereoscopic views may be compared to derive z-axis values of points on the dental object, permitting, for instance, derivation of further z-axis points within and/or around the object using interpolation. This process may be repeated with multiple dental objects in the field of view, including without limitation environmental features of interest identified by an object classifier and/or indicated by an operator.

In an embodiment, x and y axes may be chosen to span a plane common to two cameras used for stereoscopic image capturing and/or an xy plane of the first frame. As a result, x and y translational components and ¢ may be pre-populated in translational and rotational matrices for affine transformation of coordinates of the dental object, also as described above. Initial x and y coordinates and/or guesses at transformational matrices may alternatively or additionally be performed between the first frame and the second frame, as described above. For each point of a plurality of points on the dental object and/or edge and/or edges of the object as described above, x and y coordinates of a first stereoscopic frame may be populated, with an initial estimate of z coordinates based, for instance, on assumptions about the object, such as an assumption that the ground is substantially parallel to an xy plane as selected above. Z coordinates, and/or x, y, and z coordinates, registered using image capturing and/or object identification processes as described above may then be compared to coordinates predicted using an initial guess at transformation matrices. An error function may be computed by comparing the two sets of points, and new x, y, and/or z coordinates may be iteratively estimated and compared until the error function drops below a threshold level.

In some cases, the machine vision system used in the context of associating dental and medical data may employ a classifier, such as any classifier described throughout this disclosure. These classifiers can be trained to identify specific dental conditions, abnormalities, or features within the captured dental images, aiding in the prediction of related medical conditions or the identification of correlations between dental and systemic health.

As used in this disclosure, a "signal" is any intelligible representation of data, for example from one device to another. A signal may include an optical signal, a hydraulic signal, a pneumatic signal, a mechanical signal, an electric signal, a digital signal, an analog signal and the like. In the context of associating dental and medical data and predicting medical conditions using dental data, signals may be used to transmit dental images, medical records, or other relevant data between various components of the system, such as dental imaging devices, electronic health record systems, and the computing devices responsible for processing and analyzing the data.

In some cases, a signal may be used to communicate with a computing device, for example by way of one or more ports. The computing device may receive dental images, location data, or medical data through these ports, which can include USB ports, Ethernet ports, or other standard communication interfaces. In some cases, a signal may be transmitted and/or received by a computing device, for example by way of an input/output port. This allows the computing device to exchange data with external devices, such as dental scanners or medical diagnostic equipment.

An analog signal, such as an analog representation of a dental image captured by an intraoral camera, may be digitized, for example by way of an analog to digital converter. This digitization process converts the continuous analog signal into a discrete digital format suitable for processing by the computing device. In some cases, an analog signal may be processed, for example by way of any analog signal processing steps described in this disclosure, prior to digitization. This pre-processing can include noise reduction, filtering, or other techniques to improve the quality of the signal before it is converted to a digital format.

In some cases, a digital signal may be used to communicate between two or more devices, including without limitation computing devices. For example, a digital signal representing a patient's electronic health record may be transmitted from a hospital's database to the computing device responsible for associating dental and medical data. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 128 [printer port]), and the like. These protocols ensure that the digital data is transmitted accurately and efficiently between devices, enabling the seamless integration of dental and medical data for the purpose of predicting medical conditions.

Figure 2:
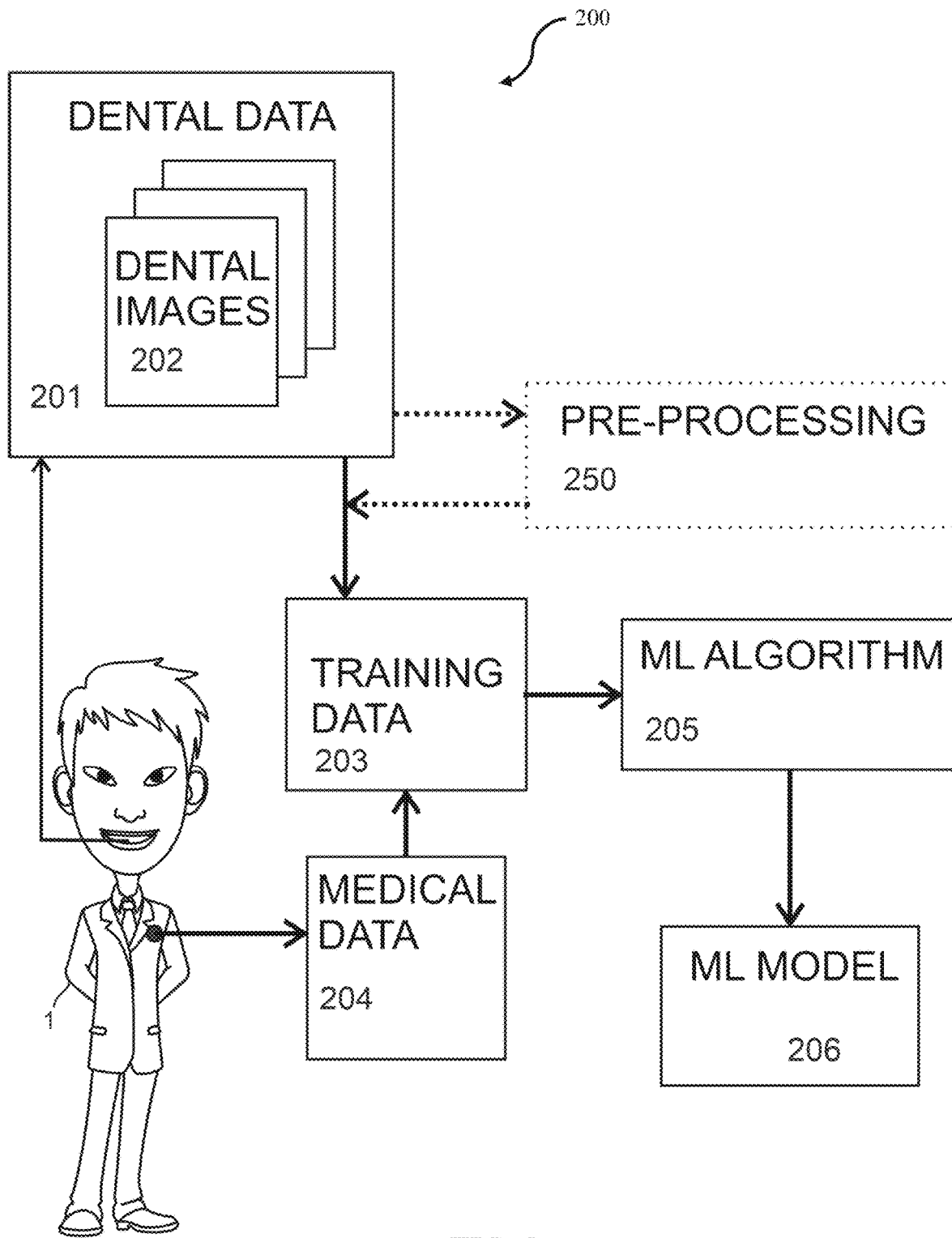
FIG. 2 is a flow diagram illustrating the training of a machine learning model to associate medical data with dental data.

Reference is now made to FIG. 2, which depicts a flow diagram illustrating an exemplary process 200 of training a machine learning model to associate medical data with dental data. The diagram showcases the key components involved in this process, including dental data 201, dental images 202, pre-processing step 250, training data 203, medical data 204, machine learning algorithm 205, and the resulting machine learning model 206.

The illustrative process begins with the acquisition of dental data 201 from User 1. Dental data 201 encompasses a wide range of information related to the user's oral health, such as dental records, dental history, and results from various dental examinations. This data may be obtained through multiple sources, including dental practice management software, electronic health record systems, and direct input from dental professionals. A vital component of dental data 201 is dental images 202. These are images typically acquired using advanced imaging techniques, such as digital radiography (X-rays), intraoral cameras, and 3D scanning devices. Dental images 202 provide detailed visual representations of the user's teeth, gums, and surrounding oral structures, allowing for a comprehensive assessment of their oral health status. The images may include panoramic X-rays, bitewing X-rays, periapical X-rays, and intraoral photographs, among others.

In preferable aspects, the dental data 201 undergoes a pre-processing step 250. During this step, the raw dental data is cleaned, normalized, and transformed into a format suitable for machine learning. Pre-processing techniques may include image enhancement, noise reduction, and segmentation to isolate specific regions of interest within the dental images. Additionally, data validation and error correction methods are applied to identify and resolve any inconsistencies or missing information in the dental records. The pre-processing step 250 is crucial for ensuring the accuracy and reliability of the subsequent machine learning process.

In addition to dental data 201, medical data 204 is obtained from User 1. Medical data 204 includes a broad spectrum of health-related information, such as the user's medical history, diagnoses, medications, laboratory test results, and vital signs. This data may be sourced from various healthcare providers, including primary care physicians, specialists, and hospitals. The integration of medical data 204 enables the establishing a comprehensive understanding of the user's overall health status and identifying potential correlations between oral health and systemic conditions. The pre-processed dental data 201 and medical data 204 are combined to form the training data 203. This training data serves as the input for the machine learning algorithm 205, which learns to recognize patterns and associations between dental and medical information. The training data 203 is carefully curated to ensure a balanced representation of various oral health conditions and their corresponding medical implications.

The machine learning algorithm 205 used in this process can vary depending on the specific requirements and complexity of the task. Common algorithms include decision trees, random forests, support vector machines, and deep learning neural networks. These algorithms are designed to automatically learn and improve their performance through exposure to large amounts of training data. They can identify intricate patterns and relationships that may be difficult for humans to discern, making them well-suited for associating dental and medical data. Through the iterative process of training, the machine learning algorithm 205 gradually refines its internal parameters and develops a robust understanding of the connections between dental and medical data. The result of this training process is the machine learning model 206, which encapsulates the learned associations and can be used to make predictions or generate insights based on new, unseen data.

The trained machine learning model 206 has the ability to associate dental data with medical data, enabling a more holistic approach to patient care. For example, the model may identify correlations between certain dental conditions, such as periodontal disease, and systemic health issues like diabetes or cardiovascular disease. By leveraging these associations, dental professionals can provide more targeted and personalized care, taking into account the patient's overall health status. Furthermore, the machine learning model 206 can assist in early detection and prevention of potential health problems. By analyzing dental images and records, the model may identify early signs of oral health issues that could have systemic implications. This enables proactive interventions and timely referrals to medical professionals when necessary, ultimately improving patient outcomes and quality of life.

With continued reference to FIG. 2, it may be provided to use user feedback to train the machine-learning models and/or classifiers described above. For example, classifier may be trained using past inputs and outputs of classifier. In some embodiments, if user feedback indicates that an output of classifier was "bad," then that output and the corresponding input may be removed from training data used to train classifier, and/or may be replaced with a value entered by, e.g., another user that represents an ideal output given the input the classifier originally received, permitting use in retraining, and adding to training data; in either case, classifier may be retrained with modified training data as described in further detail below. In some embodiments, training data of classifier may include user feedback.

With continued reference to FIG. 2, in some embodiments, an accuracy score may be calculated for classifier using user feedback. For the purposes of this disclosure, "accuracy score," is a numerical value concerning the accuracy of a machine-learning model. For example, a plurality of user feedback scores may be averaged to determine an accuracy score. In some embodiments, a cohort accuracy score may be determined for particular cohorts of persons. For example, user feedback for users belonging to a particular cohort of persons may be averaged together to determine the cohort accuracy score for that particular cohort of persons, and used as described above. Accuracy score or another score as described above may indicate a degree of retraining needed for a machine-learning model such as a classifier; a computing device on which the machine learning is performed may perform a larger number of retraining cycles for a higher number (or lower number, depending on a numerical interpretation used), and/or may collect more training data for such retraining, perform more training cycles, apply a more stringent convergence test such as a test requiring a lower mean squared error, and/or indicate to a user and/or operator that additional training data is needed.

Figure 3:
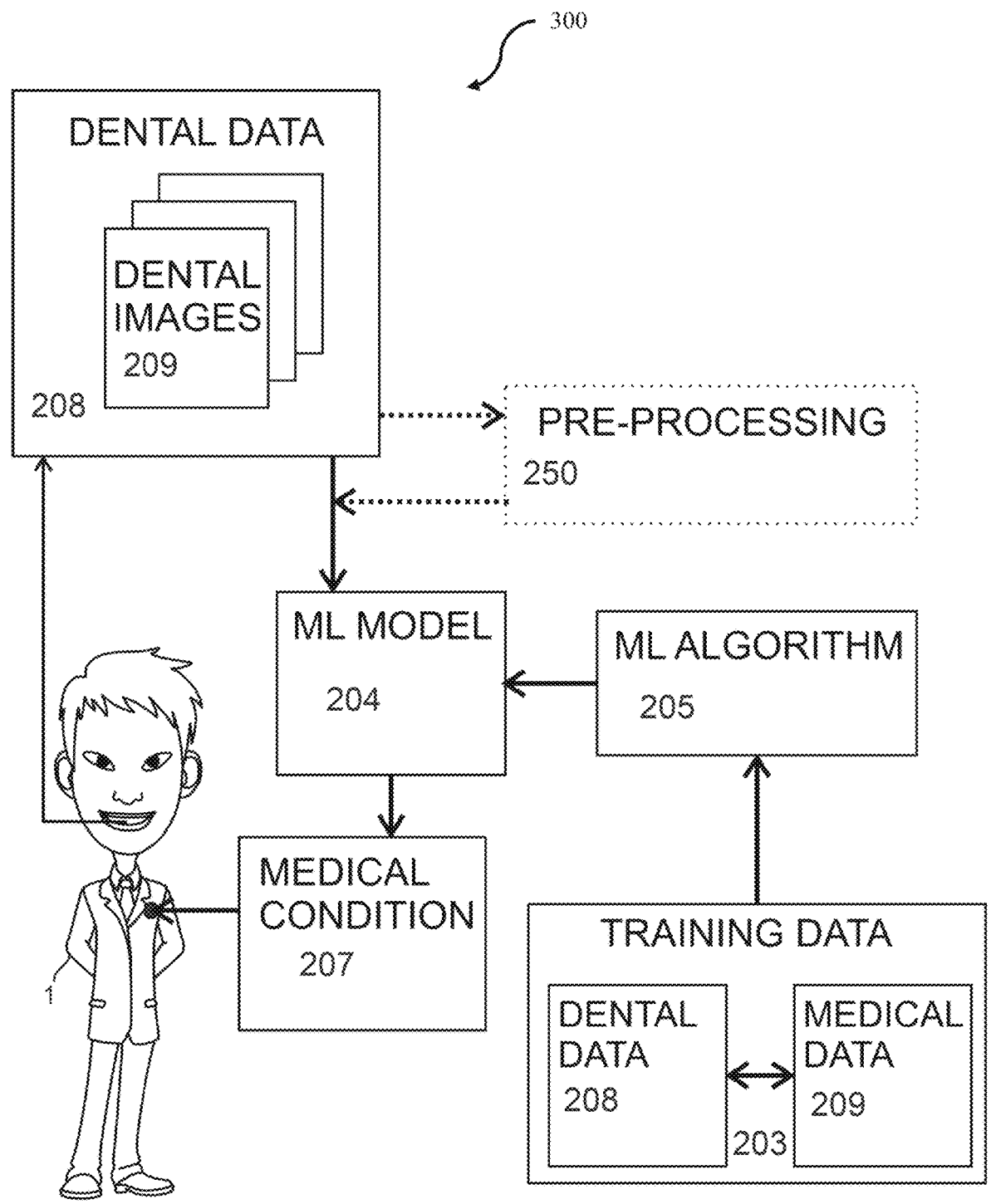
FIG. 3 is a flow diagram illustrating the prediction of a medical condition using a pre-trained machine learning model and dental data.

Referring now to FIG. 3, a flow diagram 300 illustrating the training and application of a machine learning model for associating medical data with dental data is shown. The diagram depicts the process of utilizing dental data 208 and dental images 209 from a user 1 to predict a medical condition 207 by employing a pre-trained machine learning model 206.

In one aspect, dental data 208 is acquired from user 1 during a routine dental check-up or examination. This dental data 208 may include, but is not limited to, patient demographics, dental history, oral hygiene habits, and results from various dental assessments such as periodontal charting, tooth decay indexing, and occlusal analysis. Dental images 209, which form a critical component of dental data 208, are obtained using state-of-the-art imaging modalities such as digital radiography, cone beam computed tomography (CBCT), and intraoral scanning. These dental images 209 provide high-resolution, three-dimensional visualizations of the user's teeth, gums, and surrounding oral structures, enabling a comprehensive evaluation of their oral health status.

Prior to being inputted into the machine learning model 206, the acquired dental data 208 and dental images 209 may undergo a pre-processing step 250. During this step, the raw data is cleaned, normalized, and transformed to ensure compatibility with the machine learning model's input requirements. Pre-processing techniques applied to dental data 208 may include data formatting, missing value imputation, and feature scaling. Dental images 209 may be subjected to image enhancement algorithms, such as contrast adjustment, noise reduction, and edge detection, to highlight relevant anatomical structures and pathologies. Additionally, the pre-processing step 250 may involve data augmentation techniques, such as image rotation, flipping, and cropping, to increase the diversity and robustness of the training dataset.

Illustrated in parallel to the acquisition and pre-processing of dental data 208 and dental images 209 from user 1, the machine learning model 206 is trained using a separate dataset consisting of training dental data 201 and training medical data 202. The training dental data 201 comprises a large corpus of dental records, images, and associated metadata sourced from a diverse population of patients. This data is carefully curated to ensure a balanced representation of various oral health conditions, demographics, and geographic locations. Similarly, the training medical data 202 includes a wide range of medical records, such as electronic health records (EHRs), laboratory test results, and diagnoses, which are linked to the corresponding patients in the training dental data 201.

The training dental data 201 and training medical data 202 are combined to form the comprehensive training data 203. This training data 203 serves as the input to the machine learning algorithm 205, which is responsible for learning the complex relationships and patterns between dental features and medical conditions. The choice of machine learning algorithm 205 depends on the specific nature of the problem and the characteristics of the training data 203. Common algorithms employed in this context include convolutional neural networks (CNNs) for image analysis, recurrent neural networks (RNNs) for sequence data, and decision trees or random forests for tabular data.

During the training process, the machine learning algorithm 205 iteratively adjusts its internal parameters to minimize the difference between its predictions and the ground truth labels provided in the training data 203. This process, known as optimization, allows the algorithm to learn the most informative features and patterns that are predictive of medical conditions based on dental data. Regularization techniques, such as L1/L2 regularization or dropout, may be applied to prevent overfitting and ensure the model's generalizability to unseen data.

Once the training process is complete, the resulting machine learning model 206 is capable of predicting medical conditions 207 based on input dental data 208 and dental images 209. When user 1 undergoes a dental check-up, their pre-processed dental data 208 and dental images 209 are fed into the trained machine learning model 206. The model analyzes this input data and generates a prediction of the user's likelihood of developing certain medical conditions 207, such as diabetes, cardiovascular disease, or respiratory disorders.

The machine learning model's predictions are based on the learned associations between dental features and medical conditions from the training data 203. For example, the presence of advanced periodontal disease in dental images 209 may be strongly correlated with an increased risk of diabetes, as determined by the model during training. By leveraging these learned associations, the machine learning model 206 can provide personalized, data-driven insights into the user's overall health status, enabling early detection and intervention.

Figure 4:
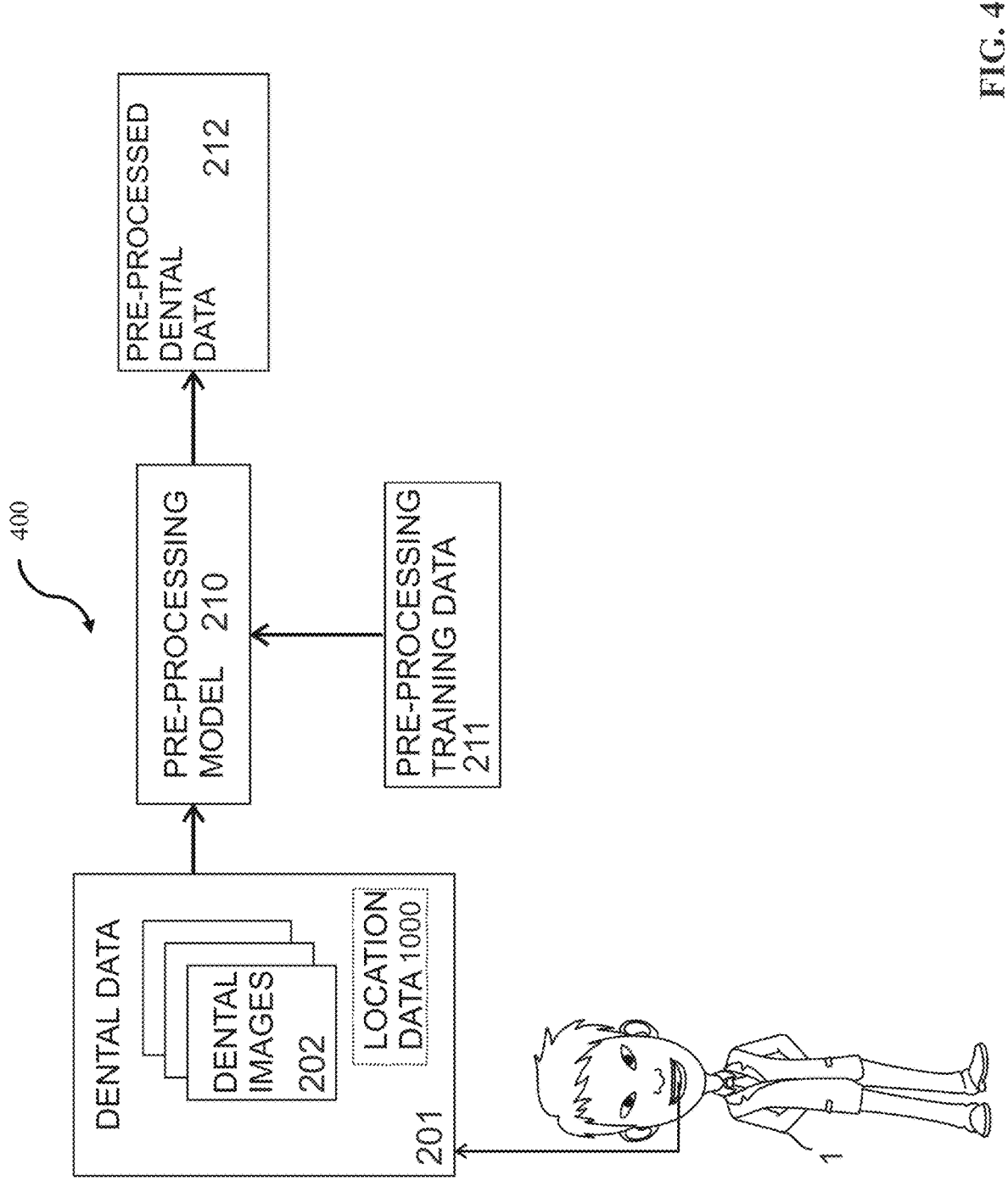
FIG. 4 is a flow diagram illustrating a 3D reconstruction process for generating pre-processed dental data using dental data.

Referring to FIG. 4, a flow diagram 400 illustrating a 3D reconstruction process for generating 3D dental images based on input dental data and a 3D model is depicted. The diagram showcases the key components involved in this process, including dental data 201, dental images 202, location data 1000, pre-processing model 210, pre-processing training data 211, and the resulting pre-processed dental data 212.

The exemplary flow process begins with the acquisition of dental data 201 from user 1. Dental data 201 comprises a comprehensive set of information related to the user's oral health, including dental images 202 and location data 1000. without limitation, dental images 202 may obtained using various imaging modalities, such as digital radiography (X-rays), intraoral cameras, and 3D scanning devices. These images provide detailed visual representations of the user's teeth, gums, and surrounding oral structures from different angles and perspectives.

In some aspects, the location data 1000 is a component of dental data 201 that enables the accurate spatial positioning and orientation of the dental images 202 within a 3D coordinate system. This location data 1000 may be obtained through various methods, such as manual landmarking by dental professionals, automatic feature detection algorithms, or the use of specialized tracking devices during image acquisition. In some illustrative aspects, location data 1000 typically includes coordinates of specific anatomical landmarks, such as tooth cusps, gingival margins, or bony structures, which serve as reference points for aligning and integrating the dental images 202 into a cohesive 3D representation.

The dental data 201, comprising dental images 202 and location data 1000, may then be passed as input to the pre-processing model 210. The pre-processing model 210 is a computational framework designed to transform the raw dental data 201 into a format suitable for 3D reconstruction. This model may employ various techniques, such as image registration, segmentation, and feature extraction, to process and prepare the dental data for subsequent steps.

To ensure the accuracy and reliability of the pre-processing model 210, it may be provided with or coupled to pre-processing training data 211. This training data 211 may consist of a large dataset of dental images, location data, and corresponding 3D reconstructions that have been manually verified and annotated by dental experts. The pre-processing model 210 learns from this training data 211 to establish the necessary mappings and transformations between the input dental data 201 and the desired 3D representation.

During the training phase, the pre-processing model 210 adjusts its internal parameters to minimize the discrepancy between its predictions and the ground truth 3D reconstructions provided in the pre-processing training data 211. This process involves iterative optimization algorithms, such as gradient descent or backpropagation, which allow the model to learn the most informative features and patterns from the training data. Regularization techniques, such as L1/L2 regularization or dropout, may be applied to prevent overfitting and ensure the model's generalizability to unseen data.

Once the pre-processing model 210 has been trained, it can be applied to new dental data 201 from user 1. The model takes the dental images 202 and location data 1000 as input and performs the necessary pre-processing steps to transform the data into a consistent and standardized format. This may involve tasks such as image cropping, resizing, normalization, and feature extraction, depending on the specific requirements of the subsequent 3D reconstruction process.

The output of the pre-processing model 210 is the pre-processed dental data 212, which represents the dental images 202 and location data 1000 in a form that is optimized for 3D reconstruction. This pre-processed data 212 may include segmented tooth regions, extracted surface meshes, or other intermediate representations that facilitate the generation of a final 3D dental model.

The pre-processed dental data 212 can then be fed into a 3D reconstruction algorithm or pipeline, which uses the information contained in the pre-processed data to create a detailed and accurate 3D representation of the user's oral cavity. This 3D reconstruction process may involve techniques such as triangulation, surface fitting, or volumetric rendering, depending on the desired level of detail and the specific application requirements.

The resulting 3D dental images provide a comprehensive and interactive visualization of the user's oral structures, enabling dental professionals to perform advanced analyses, treatment planning, and patient communication. These 3D images can be used for a wide range of applications, such as orthodontic treatment simulation, implant planning, surgical guide fabrication, and patient education.

Figure 5:
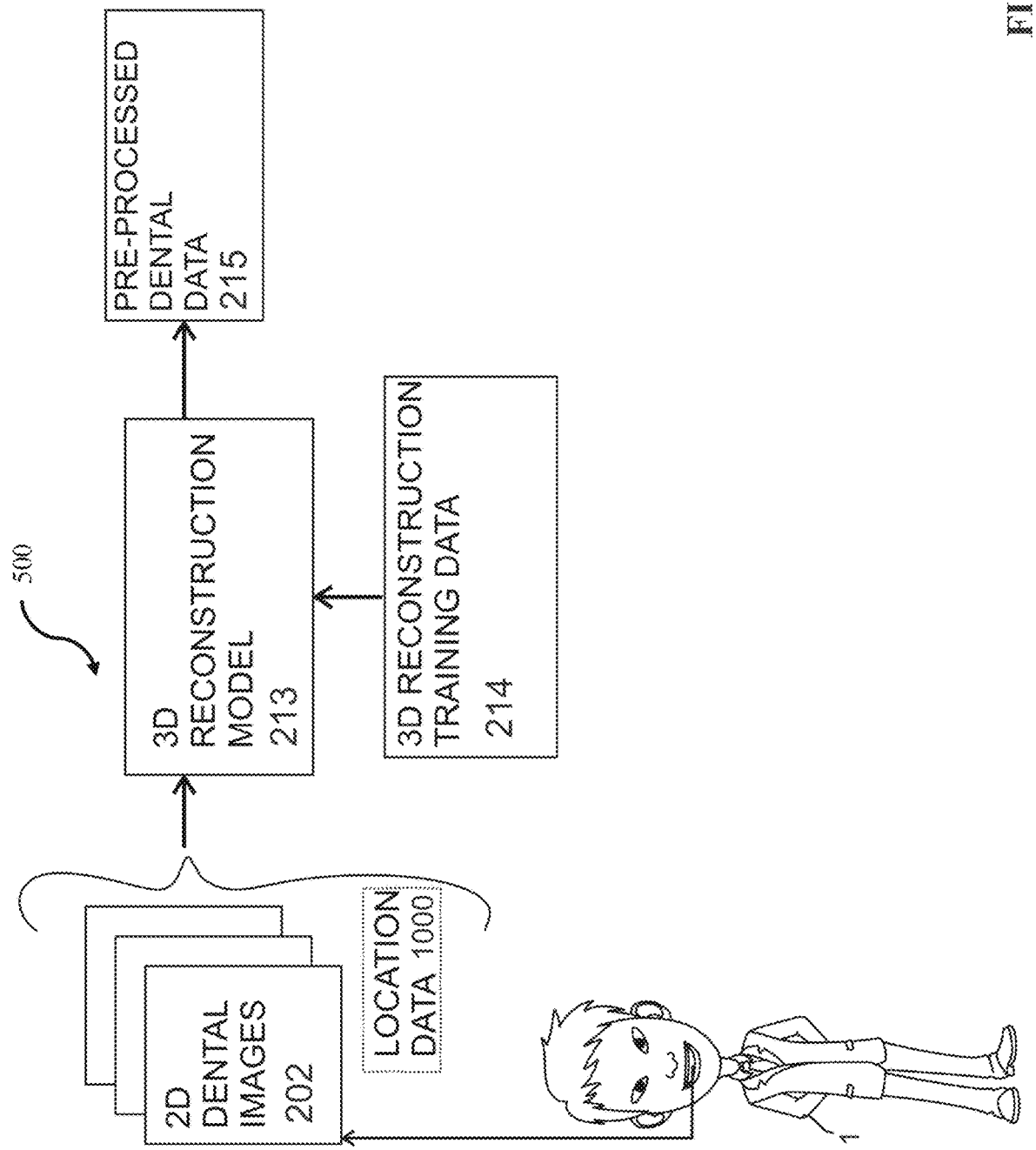
FIG. 5 is a flow diagram illustrating a 3D reconstruction process for generating pre-processed dental data using dental images, location data, a 3D reconstruction model, and 3D reconstruction training data.

Referring to FIG. 5, a flow diagram 500 illustrating a 3D reconstruction process for generating pre-processed dental data 215 based on input dental images 202, location data 1000, and a 3D reconstruction model 213 is presented. The diagram highlights components involved in this process, including dental images 202, location data 1000, 3D reconstruction model 213, 3D reconstruction training data 214, and the resulting pre-processed dental data 215.

The exemplary process commences with the acquisition of dental images 202 from user 1. These dental images 202 are obtained using various imaging modalities, such as digital radiography (X-rays), intraoral cameras, and 3D scanning devices. The dental images 202 capture detailed visual information of the user's teeth, gums, and surrounding oral structures from different angles and perspectives. In addition to the dental images 202, location data 1000 is collected for user 1. Location data 1000 may represents the spatial positioning and orientation information associated with the dental images 202. This data may be obtained through various methods, such as manual landmarking by dental professionals, automatic feature detection algorithms, or the use of specialized tracking devices during image acquisition. The location data 1000 typically includes coordinates of specific anatomical landmarks, such as tooth cusps, gingival margins, or bony structures, which serve as reference points for aligning and integrating the dental images 202 into a cohesive 3D representation.

In the context of associating dental and medical data, accurately determining the pose of the dental camera is crucial for generating precise 3D reconstructions of the oral cavity and identifying specific dental features and structures. In some cases, pose estimation may require knowledge of calibration parameters of the dental camera, specifically a camera matrix, K, and distortion coefficients. Calibration parameters may be specific to the dental camera and may remain unchanging until the camera optics are modified, for example, with a change in focus. These calibration parameters account for the intrinsic properties of the dental camera, such as focal length, principal point, and lens distortion, which influence how the 3D scene is projected onto the 2D image plane. An example intrinsic camera matrix, K, is shown below:

$$K = \begin{pmatrix} \alpha & a & x_0 \\ 0 & \alpha & y_0 \\ 0 & 0 & 1 \end{pmatrix}$$

where is the focal length of camera in terms of pixel dimensions, and (x0, y0) is a principle point on image, e.g. a point along the camera's z-axis, and s is a skew factor which is often zero for ell-corrected optics. Camera pose respect to an object can be found from a transformation from an object coordinate system to a camera coordinate system, such as a homography transform, a perspective n-point transform, and/or an affine transform. Transformation can be described as:

$$sp_c = K[R|T]p_w$$

where s is a scale factor, $p_w = [x\ y\ z\ 1]^T$ is a homogeneous world point, $p_c = [u\ v\ 1]^T$ is a corresponding homogeneous image point, K, is intrinsic camera matrix, and R and T are desired 3D rotation and 3D translation of the camera. According to some embodiments, transformation comprises a Perspective-n-Point (PnP) solution, such as solvePnPRansac method, which can be found in OpenCV's Camera Calibration and 3D Reconstruction module. solvePnPRansac further comprises RANSAC in conjunction with PnP solutions and makes the estimated pose more robust to outliers.

The dental images 202 and location data 1000 are then passed as input to the 3D reconstruction model 213. The 3D reconstruction model 213 may be a computational framework designed to process the input data and generate a 3D representation of the user's oral cavity. This model employs advanced algorithms and techniques, such as surface reconstruction, volumetric rendering, and mesh optimization, to convert the 2D dental images 202 and location data 1000 into a 3D structure.

To ensure the accuracy and reliability of the 3D reconstruction model 213, it is coupled with 3D reconstruction training data 214. The 3D reconstruction training data 214 consists of a large dataset of dental images, location data, and corresponding 3D reconstructions that have been manually verified and annotated by dental experts. This training data 214 serves as a reference for the 3D reconstruction model 213 to learn the necessary mappings and transformations between the input data and the desired 3D output.

During the training phase, the 3D reconstruction model 213 learns to extract relevant features and patterns from the dental images 202 and location data 1000, and to establish the spatial relationships between these features in a 3D space. The model adjusts its internal parameters through an iterative optimization process, such as gradient descent or backpropagation, to minimize the discrepancy between its predictions and the ground truth 3D reconstructions provided in the 3D reconstruction training data 214. Regularization techniques, such as L1/L2 regularization or dropout, may be applied to prevent overfitting and ensure the model's generalizability to unseen data.

Once the 3D reconstruction model 213 has been trained, it can be applied to new dental images 202 and location data 1000 from user 1. The model processes the input data, leveraging the learned mappings and transformations, to generate a 3D representation of the user's oral cavity. This 3D representation is output as pre-processed dental data 215.

The pre-processed dental data 215 represents a standardized and optimized form of the 3D reconstructed dental model. It may include information such as surface meshes, voxel grids, or point clouds, depending on the specific requirements of the intended application. The pre-processed dental data 215 serves as a foundation for various downstream tasks, such as dental implant planning, orthodontic treatment simulation, or the fabrication of dental prostheses.

The 3D reconstruction model 213, powered by the 3D reconstruction training data 214, enables the generation of highly accurate and detailed pre-processed dental data 215 from the input dental images 202 and location data 1000. This approach streamlines the 3D reconstruction process, reducing the need for manual intervention and ensuring consistency across different cases.

Figure 6:
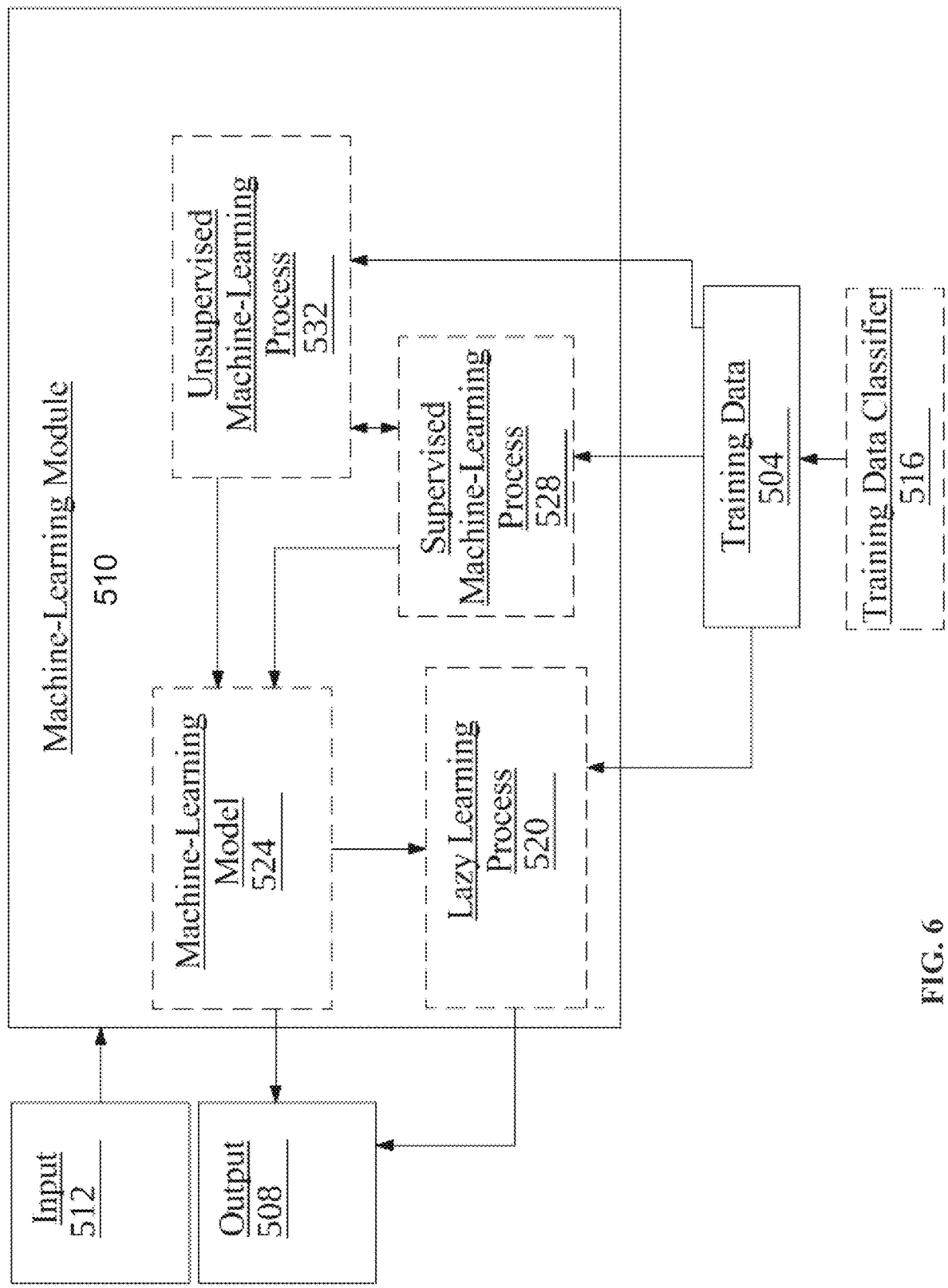
FIG. 6 depicts a exemplary machine learning module, including training data, training data classifier, supervised and unsupervised machine learning processes.

Now referring to FIG. 6, an exemplary machine learning module 510 is illustrated. The diagram depicts the key components and processes involved in the generation of a machine learning model 524 and its application to input data 512 to produce output 508. Also shown on the figure is the training data 504, which is coupled to the module 510. The training data 504 may comprise of a large dataset that has been carefully curated and prepared for the purpose of training the machine learning model 524. To ensure the quality and relevance of the training data 504, a training data classifier 216 is employed. The training data classifier 216 is responsible for categorizing and labeling the training data 504 based on predefined criteria or classes. This classification process helps to organize the training data 504 into meaningful subsets, facilitating the learning process of the machine learning model 524.

The machine learning module 510 may utilize either a supervised machine learning process 528 or an unsupervised machine learning process 532 to obtain the machine learning model 524. In a supervised learning approach, the training data 504 includes both input features and corresponding output labels or targets. The machine learning model 524 learns to map the input features to the desired outputs by minimizing the discrepancy between its predictions and the provided labels. This process allows the model to learn the underlying patterns and relationships within the training data 504, enabling it to make accurate predictions on new, unseen data.

Conversely, in an unsupervised learning approach, the training data 504 consists only of input features without any corresponding output labels. The machine learning model 524, in this case, aims to discover inherent structures, patterns, or groupings within the training data 504. Unsupervised learning techniques, such as clustering or dimensionality reduction, allow the model to explore and extract meaningful insights from the data without explicit guidance.

Regardless of the chosen learning approach, the machine learning model 524 may employ a lazy learning process to the training data 504. Lazy learning, also known as instance-based learning or non-parametric learning, is a paradigm in which the model postpones the generalization process until a new query or input is encountered. In contrast to eager learning methods, which build a general model during training, lazy learning methods store the training data 504 and defer the computation of a decision boundary or prediction until a specific query is made.

One of the key advantages of lazy learning is its ability to adapt to new data points without the need for retraining the entire model. When a new input 512 is provided to the machine learning module 510, the lazy learning process compares the input 512 to the stored training data 504 and makes predictions based on the most similar instances. This approach allows the model to handle complex and evolving datasets, as it can incorporate new information on-the-fly without requiring a complete retraining process.

Examples of lazy learning algorithms include k-Nearest Neighbors (k-NN), where the model predicts the output based on the majority class or average value of the k most similar instances in the training data 504, and Locally Weighted Regression (LWR), which assigns weights to the training instances based on their proximity to the query point and performs a weighted regression to estimate the output.

When an input 512 is provided to the machine learning module 510, it is processed by the machine learning model 524 using the lazy learning approach. The model compares the input 512 to the stored training data 504, identifies the most relevant instances, and generates an output 508 based on the patterns and relationships learned from those instances. The output 508 represents the predicted or inferred result, which can be a classification label, a regression value, or any other desired format depending on the specific application.

The machine learning module 510, with its combination of training data classification, supervised or unsupervised learning processes, and lazy learning approach, provides a powerful and flexible framework for building intelligent systems. By leveraging the vast amount of training data 504 and the ability to adapt to new inputs, the module 510 can generate accurate and reliable outputs 508, enabling a wide range of applications in various domains, such as healthcare, finance, and customer service.

Figure 7:
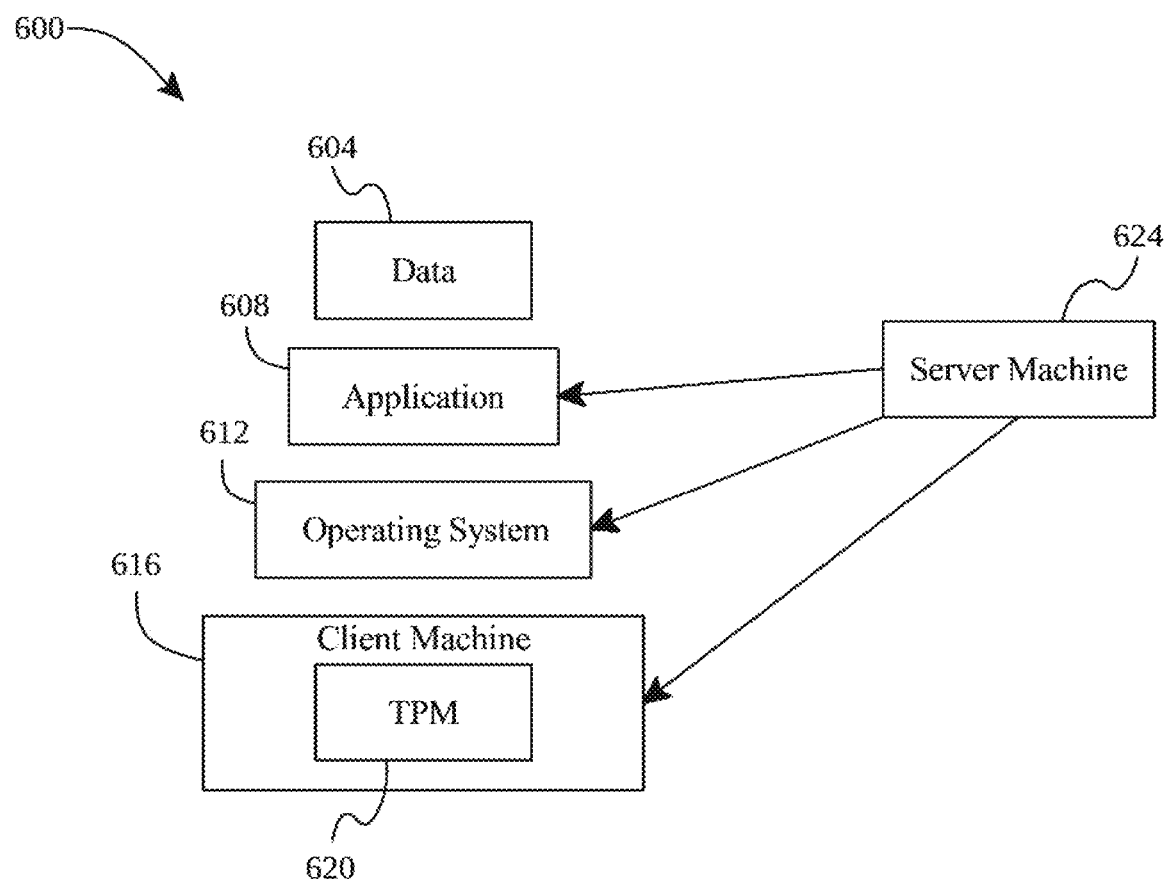
FIG. 7 illustrates a exemplary application architecture, including data, application, operating system, client machine, and server, illustrating different tiers of connection.

Referring to FIG. 7, an exemplary application architecture is depicted, illustrating the interactions between various components and tiers within a computing system. The diagram showcases the flow of data 604 through the application 608, operating system 612, and client machine 616, as well as the potential connections to a server 624. In some aspects, the data 604 represents the raw information that is processed, analyzed, and transformed by the application 608. The data 604 may originate from various sources, such as databases, sensors, user inputs, or external systems, and it serves as the input for the application's functionalities.

The application 608 is the central component of the architecture, responsible for processing the data 604 and implementing the desired functionalities. Within the application 608, machine learning algorithms may be employed to extract insights, make predictions, or automate decision-making processes. These algorithms can leverage techniques such as supervised learning, unsupervised learning, or reinforcement learning, depending on the nature of the data 604 and the specific requirements of the application 608. The application 608 may also incorporate other computational methods, such as statistical analysis, data mining, or rule-based systems, to complement the machine learning algorithms and provide a comprehensive solution.

The operating system 612 serves as the interface between the application 608 and the underlying hardware and software resources of the client machine 616. It provides essential services, such as memory management, process scheduling, and input/output operations, enabling the application 608 to execute efficiently and interact with the user and other system components. The operating system 612 also ensures proper resource allocation and security, preventing unauthorized access or malicious activities that could compromise the integrity of the application 608 or the client machine 616.

The client machine 616 represents the computing device on which the application 608 and operating system 612 reside and execute. As described in FIG. 1, the client machine 616 may encompass a wide range of devices, including personal computers, smartphones, tablets, or embedded systems. The client machine 616 provides the necessary hardware resources, such as processors, memory, storage, and input/output interfaces, to support the execution of the application 608 and the operating system 612. It also facilitates user interaction with the application 608 through various input devices, such as keyboards, mice, or touch screens, and output devices, such as displays or speakers.

Included within the client machine 616 is the Trusted Platform Module (TPM) 620. The TPM 620 may be a secure cryptoprocessor that offers hardware-based security features to enhance the overall security of the client machine 616 and the application 608. The TPM 620 may provide capabilities such as secure key storage, cryptographic operations, and integrity measurements. It can generate and store cryptographic keys, perform encryption and decryption operations, and digitally sign data to ensure its authenticity. Additionally, the TPM 620 can measure and attest to the integrity of the software running on the client machine 616, including the operating system 612 and the application 608, by comparing their current state against known-good configurations. This attestation process may help detect any unauthorized modifications or tampering attempts, enhancing the trustworthiness of the system.

The server 624 represents an external computing resource that can interact with the application architecture at various levels. The server 624 may connect to the application 608, the operating system 612, or the client machine 616, depending on the specific requirements and design of the system. At the application level, the server 624 can provide additional functionalities, such as remote data storage, processing power, or collaborative features, extending the capabilities of the application 608. At the operating system level, the server 624 can offer services like remote administration, software updates, or security patches, ensuring the smooth operation and maintenance of the client machine 616. At the client machine level, the server 624 can facilitate remote access, file sharing, or device management, enabling centralized control and monitoring of multiple client machines.

Figure 8:
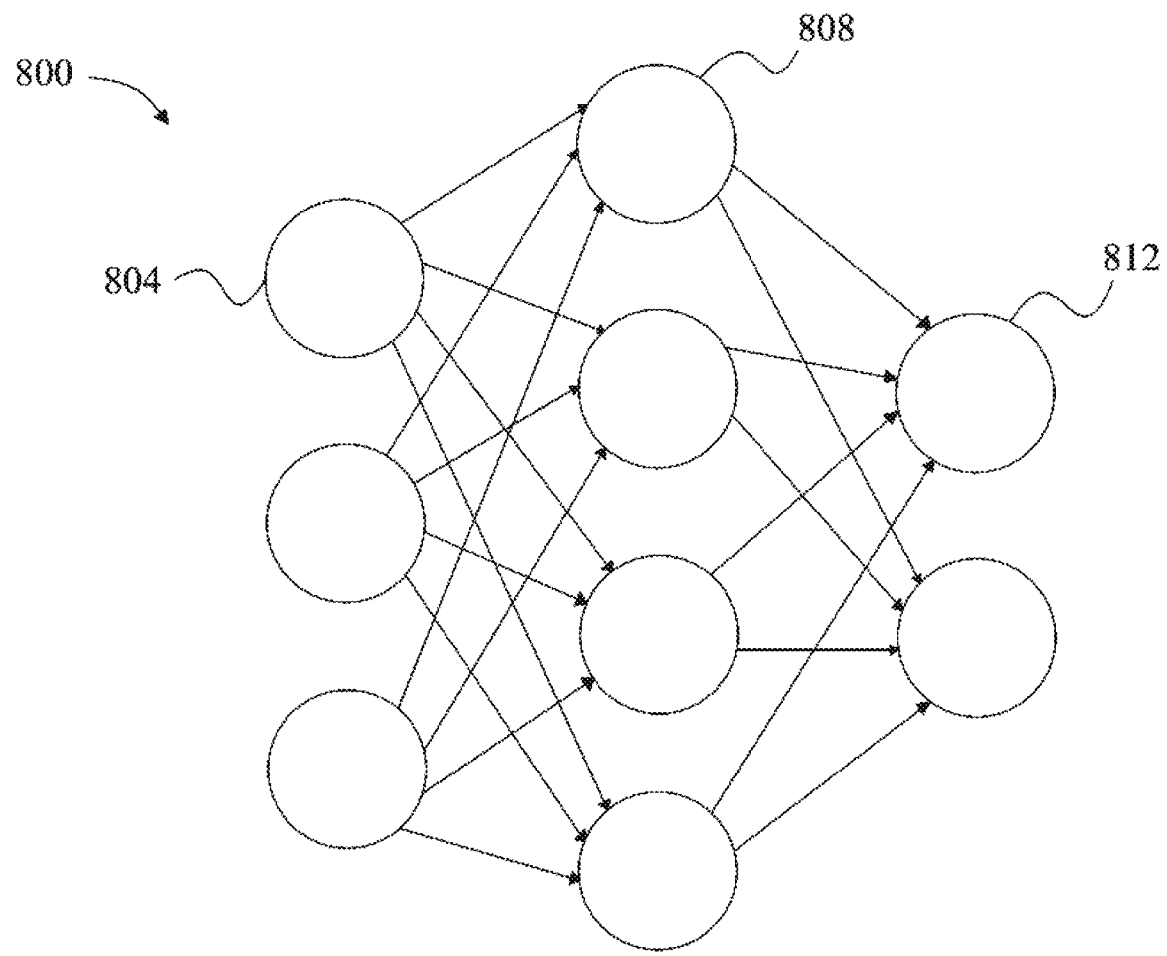
FIG. 8 depicts an exemplary embodiment of neural network according to one aspect.

Referring now to FIG. 8, an exemplary embodiment of neural network 800 is illustrated. A neural network 800 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 804, one or more intermediate layers 808, and an output layer of nodes 812. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 9:
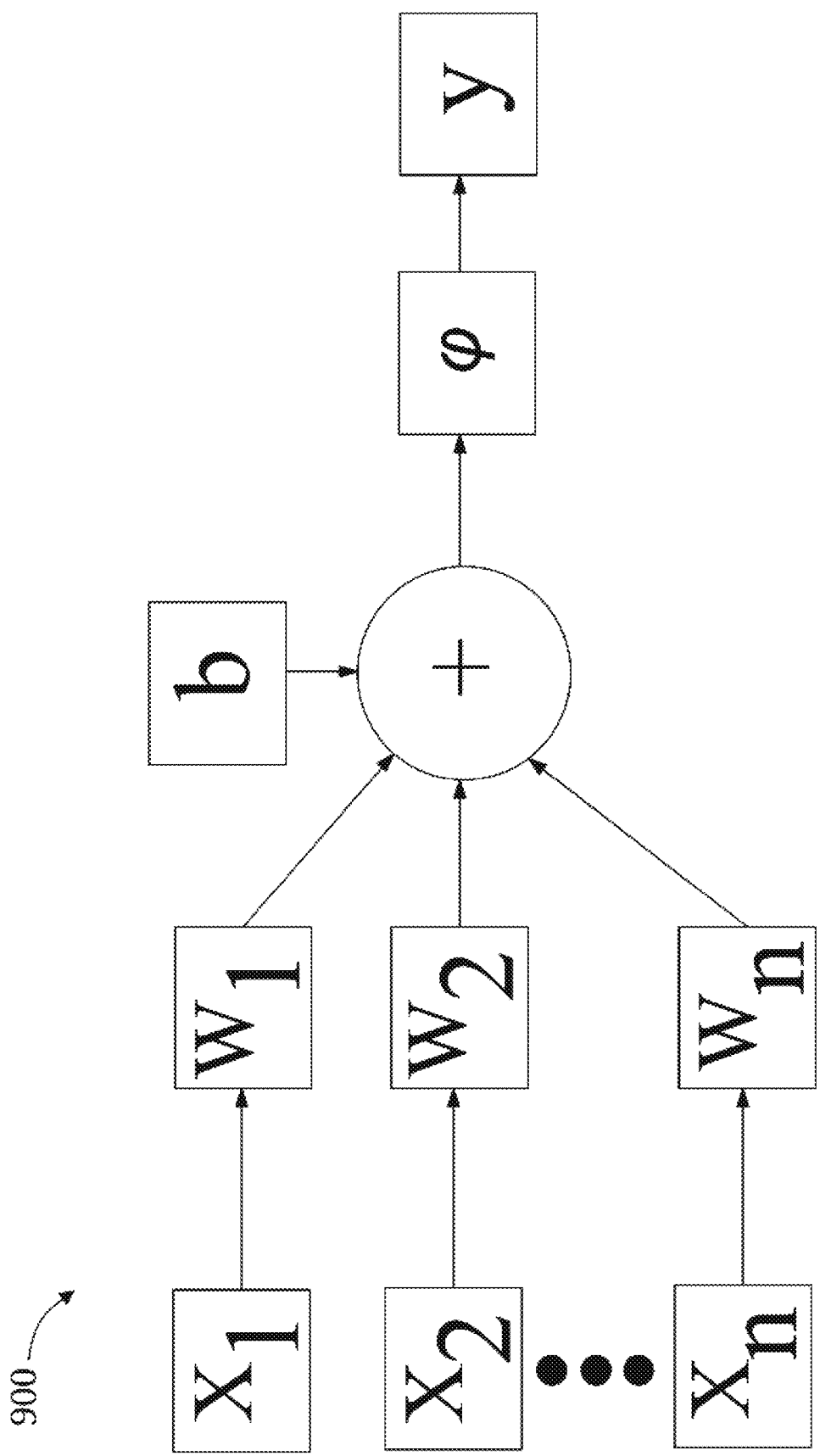
FIG. 9 depicts a neural network node according to one aspect.

Referring now to FIG. 9, an exemplary embodiment of a node 900 of a neural network is illustrated. A node may include, without limitation a plurality of inputs x, that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $ƒ(x)=\tanh^2(x)$, a rectified linear unit function such as $ƒ(x)=\max(0, x)$, a "leaky" and/or "parametric" rectified linear unit function such as $ƒ(x)=\max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $ƒ(x)=x*\text{sigmoid}(x)$, a Gaussian error linear unit function such as $f(x)=\alpha(1+\tanh(\sqrt{2/\pi}(x+bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 10:
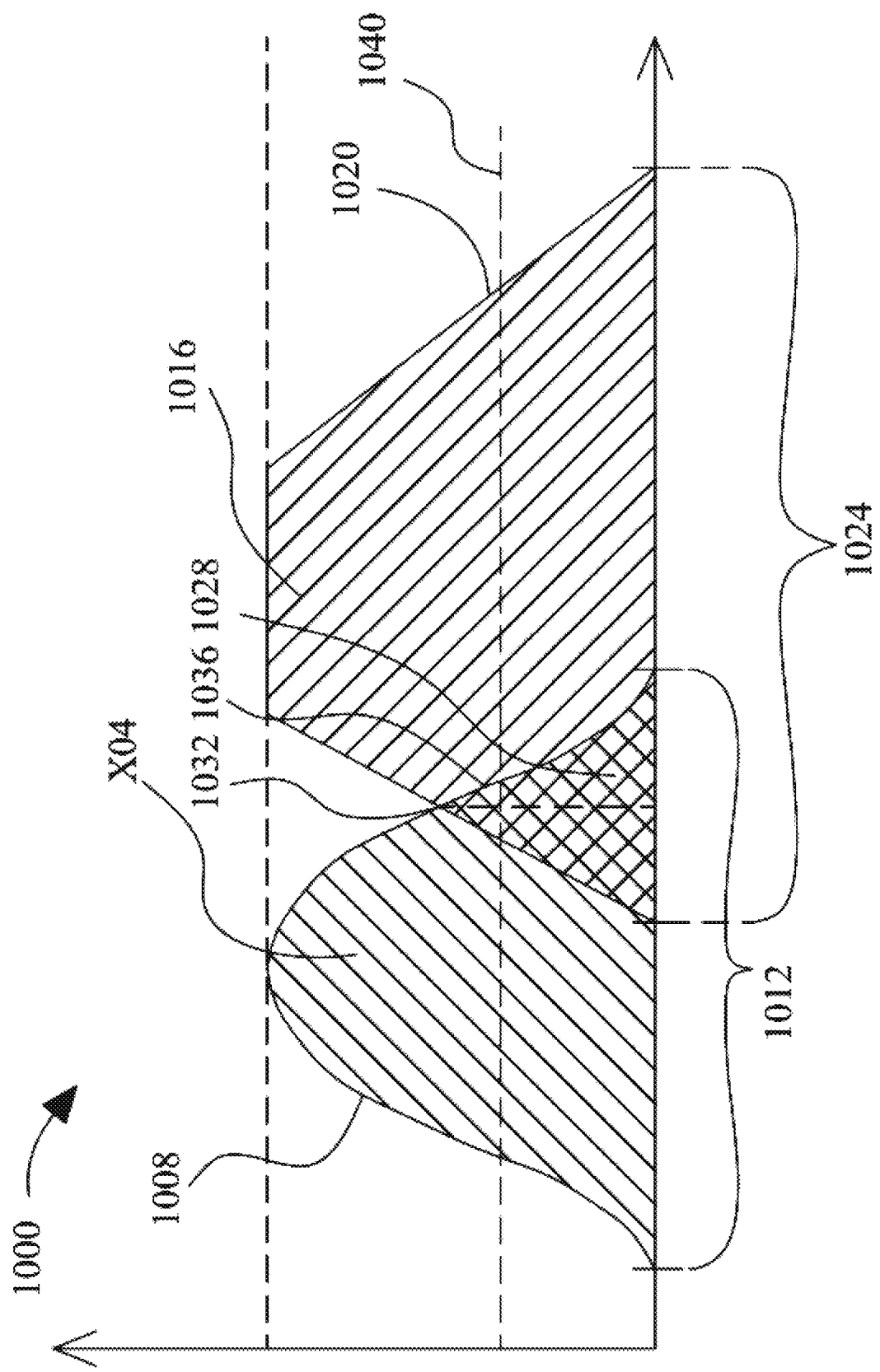
FIG. 10 is an exemplary embodiment of fuzzy set comparison.

Referring to FIG. 10, an exemplary embodiment of fuzzy set comparison 1000 is illustrated. A first fuzzy set 1004 may be represented, without limitation, according to a first membership function 1008 representing a probability that an input falling on a first range of values 1012 is a member of the first fuzzy set 1004, where the first membership function 1008 has values on a range of probabilities such as without limitation the interval [0,1], and an area beneath the first membership function 1008 may represent a set of values within first fuzzy set 1004. Although first range of values 1012 is illustrated for clarity in this exemplary depiction as a range on a single number line or axis, first range of values 1012 may be defined on two or more dimensions, representing, for instance, a Cartesian product between a plurality of ranges, curves, axes, spaces, dimensions, or the like. First membership function 1008 may include any suitable function mapping first range 1012 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, & \text{for } x > c \text{ and } x < a \\ \frac{x-a}{b-a}, & \text{for } a \leq x < b \\ \frac{c-x}{c-b}, & \text{if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 10, the first fuzzy set 1004 may represent any value or combination of values as described above, including output from one or more machine-learning models, dental images, location data, and a predetermined class, such as without limitation of medical conditions. A second fuzzy set 1016, which may represent any value which may be represented by first fuzzy set 1004, may be defined by a second membership function 1020 on a second range 1024; second range 1024 may be identical and/or overlap with first range 1012 and/or may be combined with first range via Cartesian product or the like to generate a mapping permitting evaluation overlap of first fuzzy set 1004 and second fuzzy set 1016. Where first fuzzy set 1004 and second fuzzy set 1016 have a region 1028 that overlaps, first membership function 1008 and second membership function 1020 may intersect at a point 1032 representing a probability, as defined on probability interval, of a match between first fuzzy set 1004 and second fuzzy set 1016. Alternatively or additionally, a single value of first and/or second fuzzy set may be located at a locus 1036 on first range 1012 and/or second range 1024, where a probability of membership may be taken by evaluation of first membership function 1008 and/or second membership function 1020 at that range point. A probability at 1028 and/or 1032 may be compared to a threshold 1040 to determine whether a positive match is indicated. Threshold 1040 may, in a non-limiting example, represent a degree of match between first fuzzy set 1004 and second fuzzy set 1016, and/or single values therein with each other or with either set, which is sufficient for purposes of the matching process; for instance, threshold may indicate a sufficient degree of overlap between an output from one or more machine-learning models and/or dental images, location data and a predetermined class, such as without limitation medical condition categorization, for combination to occur as described above. Alternatively or additionally, each threshold may be tuned by a machine-learning and/or statistical process, for instance and without limitation as described in further detail below.

Further referring to FIG. 10, in an embodiment, a degree of match between fuzzy sets may be used to classify dental images with medical conditions. For instance, if dental images have a fuzzy set matching a medical condition fuzzy set by having a degree of overlap exceeding a threshold, the computing device may classify the dental images as belonging to the medical condition categorization. Where multiple fuzzy matches are performed, degrees of match for each respective fuzzy set may be computed and aggregated through, for instance, addition, averaging, or the like, to determine an overall degree of match.

Still referring to FIG. 10, in an embodiment, dental images may be compared to multiple medical condition categorization fuzzy sets. For instance, dental images may be represented by a fuzzy set that is compared to each of the multiple medical condition categorization fuzzy sets; and a degree of overlap exceeding a threshold between the dental images fuzzy set and any of the multiple medical condition categorization fuzzy sets may cause the computing device to classify the dental images as belonging to a specific medical condition categorization. For instance, in one embodiment there may be two medical condition categorization fuzzy sets, representing respectively a first medical condition categorization and a second medical condition categorization. The first medical condition categorization may have a first fuzzy set; the second medical condition categorization may have a second fuzzy set; and the dental images may have a dental images fuzzy set. The computing device, for example, may compare the dental images fuzzy set with each of the first medical condition categorization fuzzy set and the second medical condition categorization fuzzy set, as described above, and classify the dental images to either, both, or neither of the first medical condition categorization or the second medical condition categorization. Machine-learning methods as described throughout may, in a non-limiting example, generate coefficients used in fuzzy set equations as described above, such as without limitation x, c, and σ of a Gaussian set as described above, as outputs of machine-learning methods. Likewise, dental images may be used indirectly to determine a fuzzy set, as the dental images fuzzy set may be derived from outputs of one or more machine-learning models that take the dental images directly or indirectly as inputs.

Still referring to FIG. 10, a computing device may use a logic comparison program, such as, but not limited to, a fuzzy logic model to determine a medical condition categorization. A medical condition categorization may include, but is not limited to, healthy, mild, moderate, severe, and the like; each such medical condition categorization may be represented as a value for a linguistic variable representing medical condition categorization or in other words a fuzzy set as described above that corresponds to a degree of severity as calculated using any statistical, machine-learning, or other method that may occur to a person skilled in the art upon reviewing the entirety of this disclosure. In other words, a given element of dental images may have a first non-zero value for membership in a first linguistic variable value such as "healthy" and a second non-zero value for membership in a second linguistic variable value such as "mild". In some embodiments, determining a medical condition categorization may include using a linear regression model. A linear regression model may include a machine learning model. A linear regression model may be configured to map data of dental images, such as degree of severity, to one or more medical condition parameters. A linear regression model may be trained using a machine learning process. A linear regression model may map statistics such as, but not limited to, quality of dental images and severity of medical conditions. In some embodiments, determining a medical condition of dental images may include using a medical condition classification model. A medical condition classification model may be configured to input collected data and cluster data to a centroid based on, but not limited to, frequency of appearance, linguistic indicators of quality, and the like. Centroids may include scores assigned to them such that quality of dental images and severity of medical conditions may each be assigned a score. In some embodiments, medical condition classification model may include a K-means clustering model. In some embodiments, medical condition classification model may include a particle swarm optimization model. In some embodiments, determining the medical condition of dental images may include using a fuzzy inference engine. A fuzzy inference engine may be configured to map one or more dental images data elements using fuzzy logic. In some embodiments, dental images may be arranged by a logic comparison program into medical condition arrangement. A "medical condition arrangement" as used in this disclosure is any grouping of objects and/or data based on severity level and/or output score. This step may be implemented as described above in FIGS. 1-6. Membership function coefficients and/or constants as described above may be tuned according to classification and/or clustering algorithms. For instance, and without limitation, a clustering algorithm may determine a Gaussian or other distribution of questions about a centroid corresponding to a given severity level, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Further referring to FIG. 10, an inference engine may be implemented according to input and/or output membership functions and/or linguistic variables. For instance, a first linguistic variable may represent a first measurable value pertaining to dental images, such as a degree of severity of a dental condition, while a second membership function may indicate a degree of severity of a medical condition, or another measurable value pertaining to dental images. Continuing the example, an output linguistic variable may represent, without limitation, a score value. An inference engine may combine rules, such as: "if the dental condition severity is 'high' and the medical condition severity is 'high', the overall severity score is 'high'"—the degree to which a given input function membership matches a given rule may be determined by a triangular norm or "T-norm" of the rule or output membership function with the input membership function, such as min (a, b), product of a and b, drastic product of a and b, Hamacher product of a and b, or the like, satisfying the rules of commutativity (T (a, b)=T (b, a)), monotonicity: (T (a, b)≤T (c, d) if a≤c and b≤d), (associativity: T (a, T (b, c))=T (T (a, b), c)), and the requirement that the number 1 acts as an identity element. Combinations of rules ("and" or "or" combination of rule membership determinations) may be performed using any T-conorm, as represented by an inverted T symbol or "⊥," such as max (a, b), probabilistic sum of a and b (a+b-a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤ c and b≤d, associativity: ⊥(a, ⊥(b, c))=⊥(⊥(a, b), c), and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

Further referring to FIG. 10, dental images to be used may be selected by user selection, and/or by selection of a distribution of output scores, such as 100% severe, 40% moderate, and 100% mild levels or the like. Each medical condition categorization may be selected using an additional function such as severity as described above.

Figure 11:
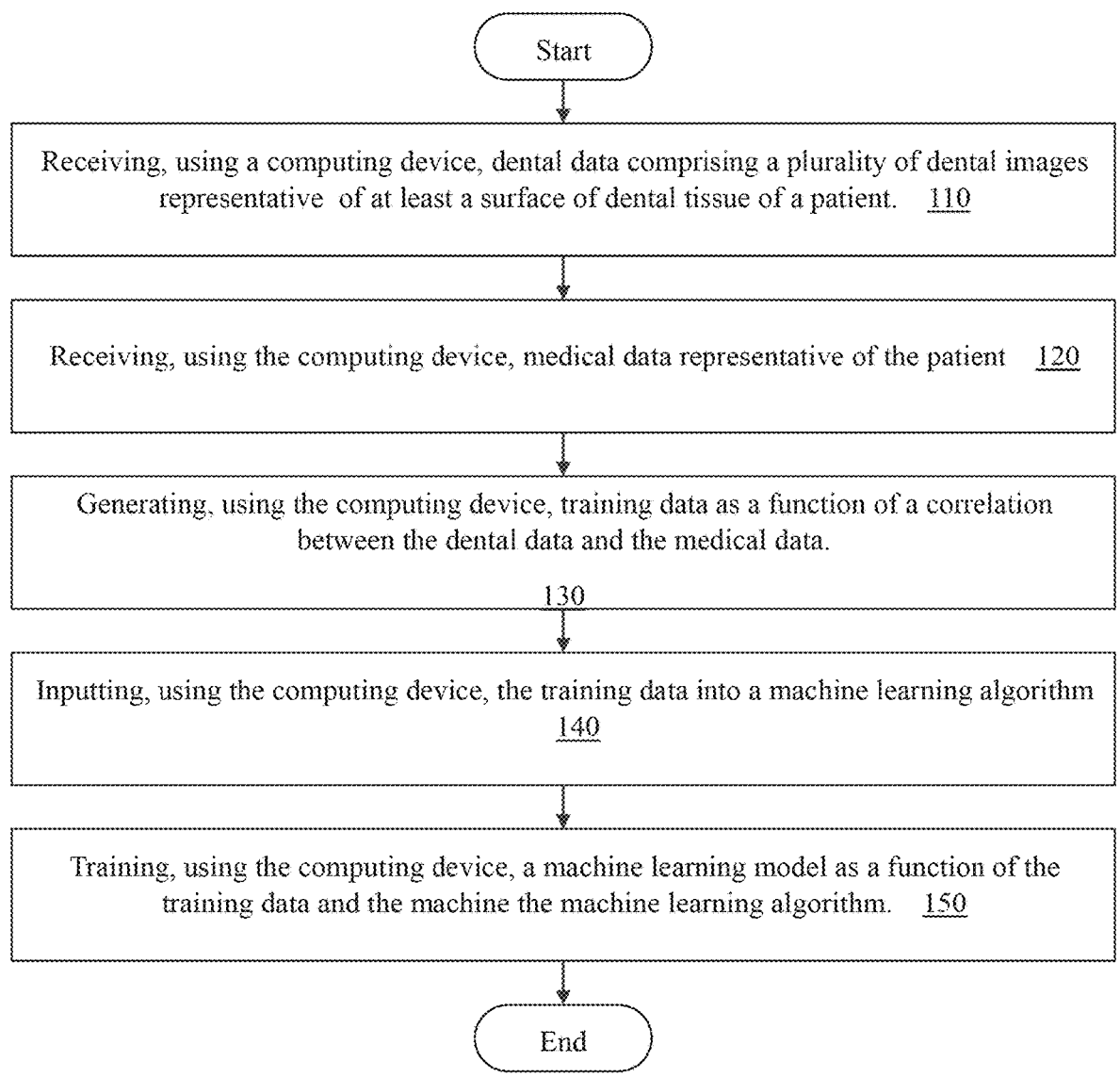
FIG. 11 is a flowchart illustrating a method of associating dental and medical data, according to some embodiments of the present disclosure.

FIG. 11 is a flowchart that describes a method of associating dental and medical data, according to some embodiments of the present disclosure. In some embodiments, at 110, the method may include receiving, using a computing device, dental data comprising a plurality of dental images representative of at least a surface of dental tissue of a patient. At 120, the method may include receiving, using the computing device, medical data representative of the patient. At 130, the method may include generating, using the computing device, training data as a function of a correlation between the dental data and the medical data. At 140, the method may include inputting, using the computing device, the training data into a machine learning algorithm. At 150, the method may include, training, using the computing device, a machine learning model as a function of the training data and the machine learning algorithm.

In some embodiments, the dental tissue may comprise one or more of dental hard tissue and dental soft tissue. In some embodiments, the dental images may comprise at least a two-dimensional digital color image representing the at least a surface of the dental tissue. In some embodiments, the dental images may additionally comprise at least a three-dimensional image representing the at least a surface of the dental tissue.

In some embodiments, the medical data may comprise one or more of radiological images, pathological test results, electronic health records, and ECG data. In some embodiments, Pre-processing the dental images comprises inputting the dental images into a pre-processing machine learning model. Pre-processing the dental images as a function of the pre-processing machine learning model and the dental images. In some embodiments, the pre-processing machine learning model comprises one or more of a transformer-based machine learning model, a classifier, and a neural network.

Figure 12:
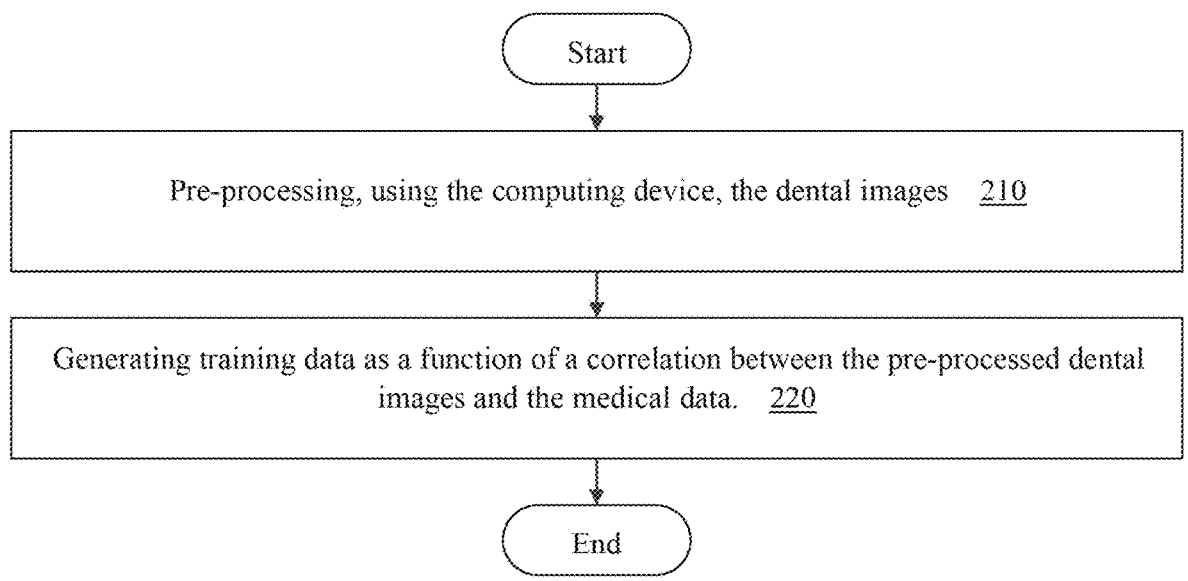
FIG. 12 is a flowchart further illustrating the method from FIG. 11.

FIG. 12 is a flowchart that further describes the method of associating dental and medical data from FIG. 11, according to some embodiments of the present disclosure. In some embodiments, at 210, the method may include, pre-processing, using the computing device, the dental images. At 220, the method may include generating the training data as a function of a correlation between the pre-processed dental images and the medical data. In some embodiments, the pre-processing machine learning model may comprise a 3D reconstruction model. Pre-processing the dental images further comprises, the method may include performing one or more additional steps. In some embodiments, the dental data may further comprise location data associated with the relative location of the at least a two-dimensional digital color image. Pre-processing the dental images further comprises, the method may include performing one or more additional steps.

Figure 13:
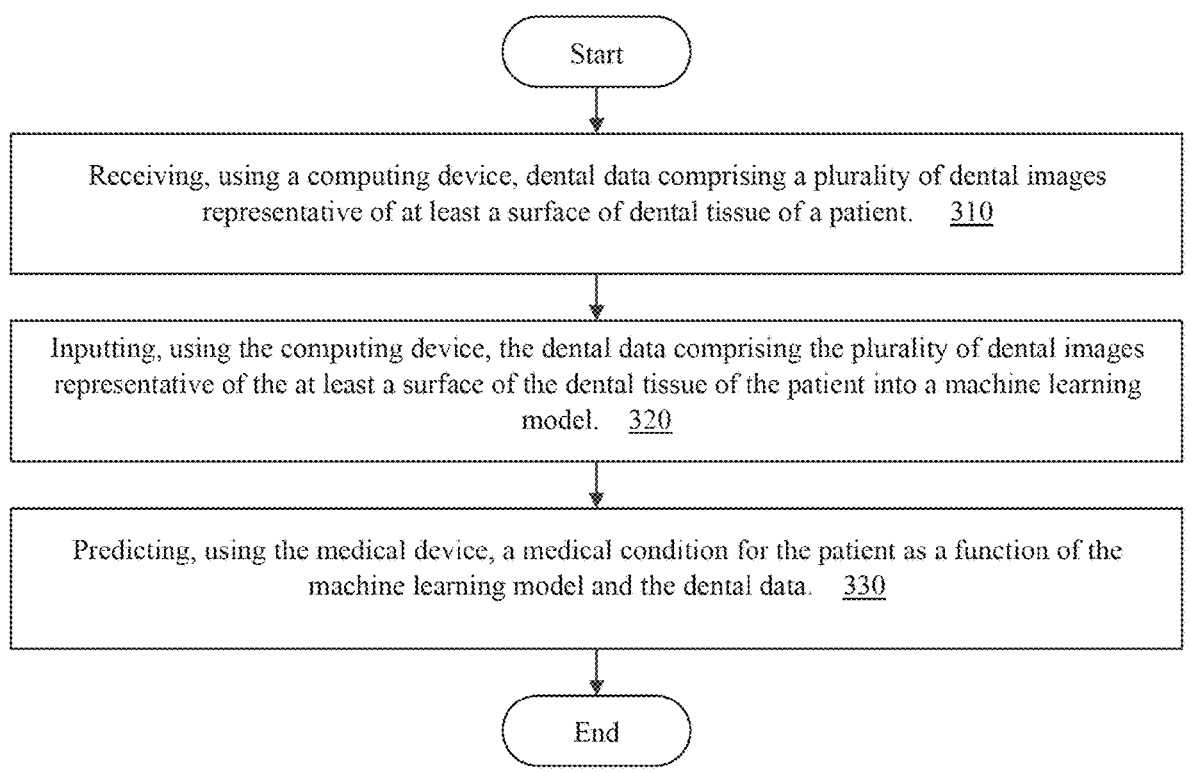
FIG. 13 is a flowchart illustrating a method of predicting a medical condition, according to some embodiments of the present disclosure.

FIG. 13 is a flowchart that describes a method of predicting a medical condition, according to some embodiments of the present disclosure. In some embodiments, at 310, the method may include receiving, using a computing device, dental data comprising a plurality of dental images representative of at least a surface of dental tissue of a patient. At 320, the method may include inputting, using the computing device, the dental data comprising the plurality of dental images representative of the at least a surface of the dental tissue of the patient into a machine learning model. At 330, the method may include predicting, using the medical device, a medical condition for the patient as a function of the machine learning model and the dental data. The machine learning model may have been trained as function of training data comprising sets of dental images correlated with sets of medical data.

Figure 14:
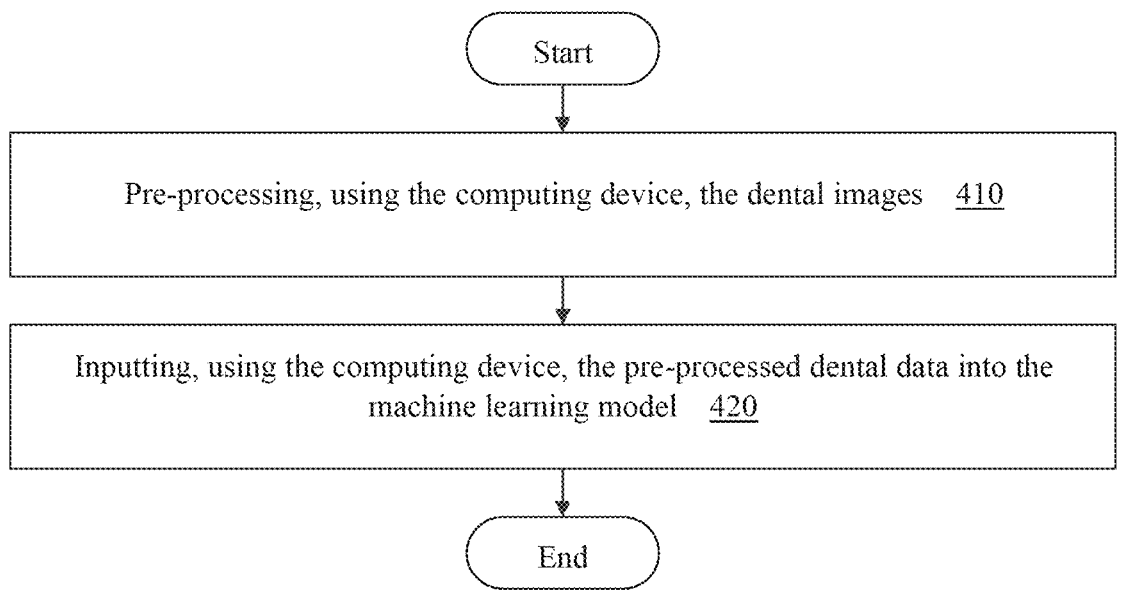
FIG. 14 is a flowchart further illustrating the method from FIG. 13.

FIG. 14 is a flowchart that further describes the method of predicting a medical condition from FIG. 13, according to some embodiments of the present disclosure. In some embodiments, at 410, the method may include, pre-processing, using the computing device, the dental images. At 420, the method may include inputting, using the computing device, the pre-processed dental data into the machine learning model. Predicting the medical condition for the patient as a function of the machine learning model and the pre-processed dental data. In some embodiments, Pre-processing the dental images comprises inputting the dental images into a pre-processing machine learning model. Pre-processing the dental images as a function of the pre-processing machine learning model and the dental images. In some embodiments, the pre-processing machine learning model comprises one or more of a transformer-based machine learning model, a classifier, and a neural network.

Figure 15:
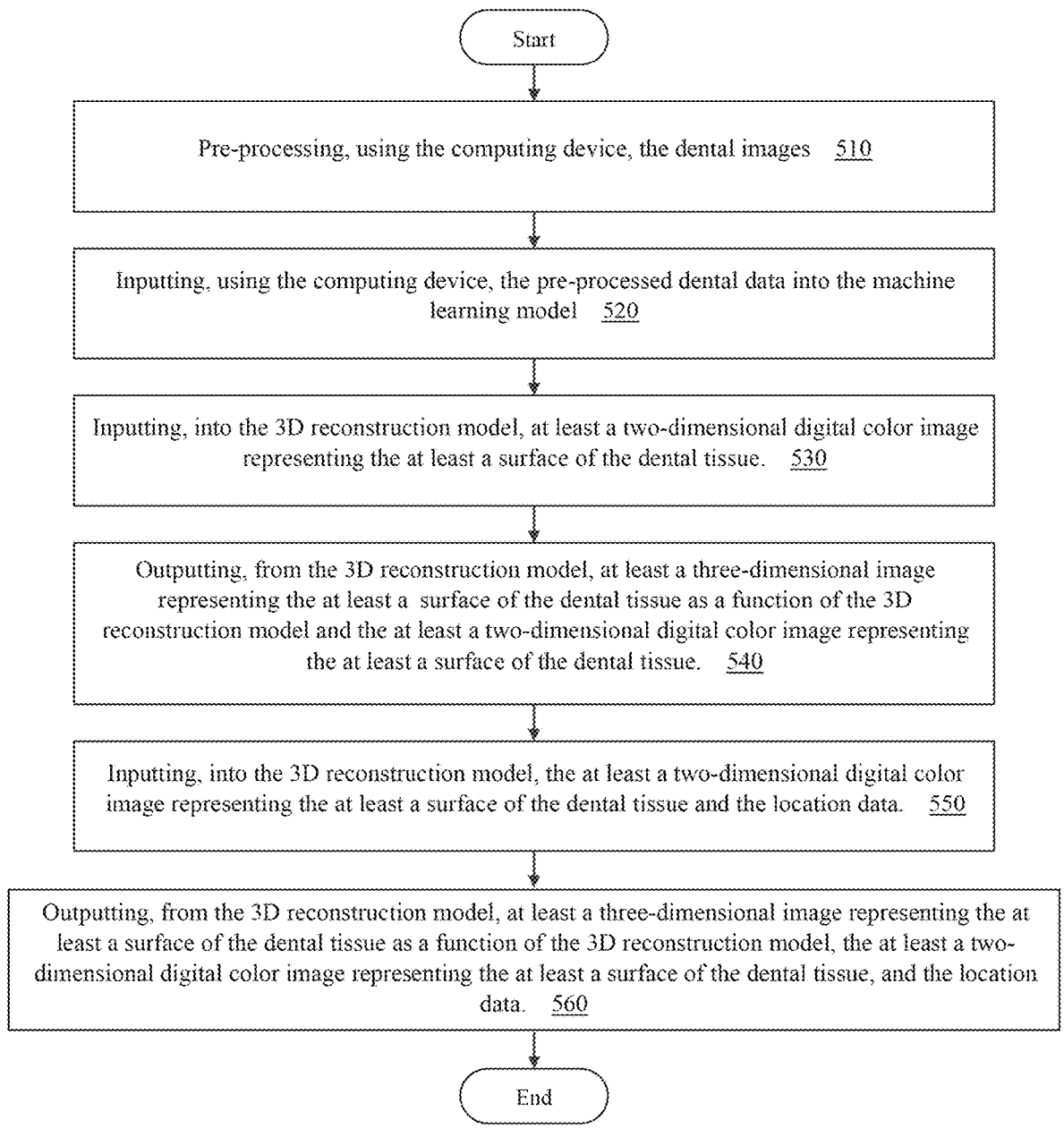
FIG. 15 is a flowchart further illustrating the method of predicting a medical condition from FIG. 13, according to some embodiments of the present disclosure.

FIG. 15 is a flowchart that further describes the method of predicting a medical condition from FIG. 13, according to some embodiments of the present disclosure. In some embodiments, at 510, the method may include pre-processing, using the computing device, the dental images. At 520, the method may include inputting, using the computing device, the pre-processed dental data into the machine learning model for predicting the medical condition for the patient as a function of the machine learning model and the pre-processed dental data. In some embodiments, the pre-processing machine learning model may comprise a 3D reconstruction model. Pre-processing the dental images further comprises the method may include, at 530, inputting, into the 3D reconstruction model, at least a two-dimensional digital color image representing the at least a surface of the dental tissue. At 540, the method may include outputting, from the 3D reconstruction model, at least a three-dimensional image representing the at least a surface of the dental tissue as a function of the 3D reconstruction model and the at least a two-dimensional digital color image representing the at least a surface of the dental tissue. In some embodiments, the dental data may further comprise location data associated with the relative location of the at least a two-dimensional digital color image. Pre-processing the dental images further comprises the method may include, at 550, inputting, into the 3D reconstruction model, the at least a two-dimensional digital color image representing the at least a surface of the dental tissue and the location data. At 560, the method may include outputting, from the 3D reconstruction model, at least a three-dimensional image representing the at least a surface of the dental tissue as a function of the 3D reconstruction model, the at least a two-dimensional digital color image representing the at least a surface of the dental tissue, and the location data.

The foregoing has been a detailed description of illustrative embodiments of the invention related to associating dental and medical data and predicting medical conditions using dental data and machine learning techniques. Various modifications and additions can be made without departing from the spirit and scope of this invention. Features of each of the various embodiments described above may be combined with features of other described embodiments as appropriate in order to provide a multiplicity of feature combinations in associated new embodiments. For example, the pre-processing techniques, machine learning models, and prediction methods from different embodiments may be combined to create new systems and methods tailored to specific dental and medical data integration scenarios. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. For instance, the order of receiving dental and medical data, generating training data, training machine learning models, and predicting medical conditions may be varied as needed to suit specific implementations. Accordingly, this description is meant to be taken only by way of example, and not to otherwise limit the scope of this invention.

Exemplary embodiments related to systems and methods for associating dental and medical data and predicting medical conditions using dental data and machine learning techniques have been disclosed above and illustrated in the accompanying drawings. It will be understood by those skilled in the art that various changes, omissions and additions may be made to that which is specifically disclosed herein without departing from the spirit and scope of the present invention. For example, alternative pre-processing techniques, machine learning architectures, and prediction methods may be employed without deviating from the core principles of the invention. Additionally, the invention may be adapted to integrate and analyze other types of healthcare data beyond dental and medical records, such as genetic data or lifestyle information, to further enhance its predictive capabilities.

In some aspects, the database used in the system for associating dental and medical data, as well as predicting medical conditions using dental data and machine learning techniques, may be implemented in various ways to store, retrieve, and organize the relevant information efficiently. The choice of database implementation depends on factors such as the volume and complexity of the data, performance requirements, scalability needs, and the specific use case within the application.

One common approach is to use a relational database, where data is organized into tables with predefined schemas and relationships between tables are established using primary and foreign keys. In this context, separate tables could be created for dental data (e.g., dental images, location data), medical data (e.g., medical records, diagnoses), and machine learning models (e.g., model parameters, training data references). The tables would be linked using appropriate keys to maintain the associations between dental and medical data, as well as the connections to the relevant machine learning models.

Alternatively, a key-value retrieval database, such as a NoSQL database, could be employed. NoSQL databases offer flexibility in handling unstructured or semi-structured data, making them suitable for storing complex data types like dental images or 3D reconstructions. In this case, dental and medical data could be stored as key-value pairs, with the keys serving as unique identifiers and the values containing the actual data or references to the data stored elsewhere.

Another option is to use a distributed data storage protocol and/or data structure, such as a distributed hash table. This approach is particularly useful when dealing with large-scale data and the need for high availability and fault tolerance. Distributed hash tables allow data to be spread across multiple nodes in a network, enabling efficient retrieval and load balancing.

Regardless of the specific database implementation, the data entries in the database may be flagged with or linked to additional elements of information. For instance, dental images could be tagged with metadata such as patient ID, date of acquisition, and the associated medical conditions. These metadata elements can be stored in separate columns within a relational database table or as additional key-value pairs in a NoSQL database.

Furthermore, the database may include data entries and/or records that are linked to one or more additional elements of information, which can be reflected in data entry cells and/or linked tables. In a relational database, this could be achieved through the use of foreign keys that establish relationships between tables. For example, a table containing dental data could have a foreign key referring to the patient ID in a separate patient information table, allowing for the retrieval of all relevant data for a specific patient.

Persons skilled in the art, upon reviewing the entirety of this disclosure, will be aware of various ways in which data entries in a database may store, retrieve, organize, and/or reflect data and/or records consistently with this disclosure. The choice of database implementation and structure will depend on the specific requirements of the application, such as data volume, performance needs, and the complexity of the relationships between dental and medical data.

Definitions of Terms

Following paragraphs include some definitions and explanations of terms to aid in understanding this disclosure. As used in this disclosure, "dental data" is information related to or representative of dental tissue, for example dental tissue of a patient.

As used in this disclosure, a "dental image" is an image representative of dental material, e.g., dental hard tissue, dental soft tissue, or the like.

As used in this disclosure, "medical data" is any information that represents at least a medical phenomenon, for instance, electronic health records, radiological images, pathological test results, or the like.

As used in this disclosure, "dental hard tissue" is hard tissue within the mouth, including osseous tissue, dentin, cementum, and enamel.

As used in this disclosure, "dental soft tissue" is soft tissue within the mouth and includes mucosa, gums, lips, and tongue.

Examples of two-dimensional digital color images include bitmap images and vector-based images. Exemplary file extension for two-dimensional digital color images include without limitation .gif, jpeg, .svg, and the like.

Examples of three-dimensional digital images include solid-body images and mesh images. Exemplary file extension for three-dimensional images include, without limitation, .stl.

As described in this disclosure, "radiological images" include any images which represent radiation (i.e., waves), for example without limitation X-ray images, CT scans, MRIs, ultrasonic images, and the like.

As used in this disclosure, a "pathological test result" includes any medical test performed on a patient. Exemplary pathological tests include without limitation blood tests, urine tests, stool tests, tissue histological analysis, and the like.

As used in this disclosure, an "electronic health record" is any electronic or digital representation of a patient's health and may include without limitation both structured data (e.g., date of birth) and unstructured data (e.g., physician notes).

As used in this disclosure, "pre-processing" refers to a processing step (e.g., for data, signals, or the like) which occurs prior to another step, such as algorithmic processing or correlation.

As used in this disclosure, a "pre-processing machine learning model" is any machine learning model, for instance any machine learning model described in this disclosure, that is used to process data, signals, or the like prior to another step described in this disclosure.

Exemplary non-limiting pre-processing machine learning models include classifiers which classify data into at least a class. Exemplary classifiers include algorithms which categorize dental data as representative of a dental condition or pathology. For instance without limitation a classifier may determine as a function of dental data that the dental tissue represented by the data likely has a dental condition, such as periodontal disease, advanced dental attrition, bruxism, orthodontic conditions, or the like. In some cases, a classifier may determine surface-by-surface presence or absence of dental conditions. For instance, in some cases, a classifier may take as inputs dental images showing surfaces of a tooth. The classifier may classify each surface as either having or not having a dental restoration on that surface. The classifier may be run on dental images showing a plurality of teeth, for instance an entire arch or mouth, and the classifier may automatically chart the locations of dental restorations in the mouth. Additional examples of possible pre-processing machine learning models include any and all machine learning process described in the co-invented and co-owned U.S. patents application Ser. Nos. 18/093,298 ("SYSTEMS AND METHODS FOR ESTIMATING A TREND ASSOCIATED WITH DENTAL TISSUE"), Ser. No. 18/093,305 ("SYSTEMS AND METHODS FOR DENTAL TREATMENT AND REMOTE OVERSIGHT"), Ser. No. 18/093,307 ("SYSTEMS AND METHODS FOR DENTAL TREATMENT AND VERIFICATION"), and Ser. No. 18/093,309 ("SYSTEMS AND METHODS FOR GENERATING AN IMAGE REPRESENTATIVE OF ORAL TISSUE CONCURRENTLY WITH DENTAL PREVENTATIVE LASER TREATMENT") each of which were filed on Jan. 4, 2023 and each of which are incorporated herein by reference in its entirety.

As used in this disclosure, "3D reconstruction model" comprises a model and/or algorithm which takes as input at least a two-dimensional digital image and outputs at least a three-dimensional image. In some cases, 3D reconstruction model may be context-aware. For instance, in some cases, 3D reconstruction model may be trained using images of dental tissue. Exemplary 3D reconstruction model is pix2vox, pix2vox++, and the like.

As used in this disclosure, "location data" is information or signals which represent position, velocity, or acceleration. Location data may be sensed by at least a location sensor, for example an inertial measurement unit and/or an optical sensor. In some cases, location data may be measured from an inertial measurement unit (IMU). IMU may be positioned for instance on a device which detects dental data for instance an intraoral hand piece configured to detect images. Alternatively or additionally, location data may be detected from an optical sensor. For instance, in some cases, location data may be derived from at least a digital dental image to determine a pose of a camera relative dental tissue.

INDUSTRIAL APPLICATION

The systems and methods for associating dental and medical data, as well as predicting medical conditions using dental data and machine learning techniques, have a wide range of applications in the healthcare industry. In dental practices, these systems can be used to identify potential systemic health issues in patients based on their dental records, enabling early intervention and preventive care. The ability to predict medical conditions from dental data can help dentists provide more comprehensive and holistic treatment plans. In medical settings, such as hospitals and clinics, the integration of dental and medical data can facilitate better communication and collaboration between dental and medical professionals, leading to improved patient outcomes. The machine learning models" ability to uncover hidden patterns and correlations between oral and overall health makes these systems suitable for use in research institutions, advancing understanding of the complex interactions between various aspects of human health. Further, the modular nature of the invention, with its adaptability to new dental imaging technologies and medical data types, ensures its relevance and applicability across diverse sectors of the healthcare industry.

Numbered Paragraphs

A1. A system for predicting a medical condition using dental data, the system comprising:
a processor; and
a memory containing instructions that instruct the processor to:
receive dental data comprising a plurality of dental images representative of at least a surface of dental tissue of a patient;
input the dental data comprising the plurality of dental images representative of the at least a surface of the dental tissue of the patient into a machine learning model, wherein the machine learning model has been trained as function of training data comprising sets of dental images correlated with sets of medical data; and
predict a medical condition for the patient as a function of the machine learning model and the dental data.

A2. The system of paragraph A1, wherein the dental tissue comprises one or more of dental hard tissue and dental soft tissue.

A3. The system of paragraph A1, wherein the dental images comprise at least a two-dimensional digital color image representing the at least a surface of the dental tissue.

A4. The system of paragraph A3, wherein the dental images additionally comprise at least a three-dimensional image representing the at least a surface of the dental tissue.

A5. The system of paragraph A1, wherein the medical data comprises one or more of radiological images, pathological test results, electronic health records, and ECG data.

A6. The system of paragraph A1, wherein the memory contains further instructions that instruct the processor to:
pre-process the dental images; and
inputting the pre-processed dental data into the machine learning model; and
wherein predicting the medical condition for the patient as a function of the machine learning model and the pre-processed dental data.

A7. The system of paragraph A6, wherein pre-processing the dental images comprising inputting the dental images into a pre-processing machine learning model; and
pre-processing the dental images as a function of the pre-processing machine learning model and the dental images.

A8. The system of paragraph A7, wherein the pre-processing machine learning model comprises one or more of a transformer-based machine learning model, a classifier, and a neural network.

A9. The system of paragraph A6, wherein the pre-processing machine learning model comprises a 3D reconstruction model; and
pre-processing the dental images further comprises:
inputting, into the 3D reconstruction model, at least a two-dimensional digital color image representing the at least a surface of the dental tissue; and
outputting, from the 3D reconstruction model, at least a three-dimensional image representing the at least a surface of the dental tissue as a function of the 3D reconstruction model and the at least a two-dimensional digital color image representing the at least a surface of the dental tissue.

A10. The system of paragraph A9, wherein the dental data further comprises location data associated with the relative location of the at least a two-dimensional digital color image; and
pre-processing the dental images further comprises:
inputting, into the 3D reconstruction model, the at least a two-dimensional digital color image representing the at least a surface of the dental tissue and the location data; and
outputting, from the 3D reconstruction model, at least a three-dimensional image representing the at least a surface of the dental tissue as a function of the 3D reconstruction model, the at least a two-dimensional digital color image representing the at least a surface of the dental tissue, and the location data.

A11. A method of predicting a medical condition using dental data, the method comprising:
receiving, using a computing device, dental data comprising a plurality of dental images representative of at least a surface of dental tissue of a patient;
inputting, using the computing device, the dental data comprising the plurality of dental images representative of the at least a surface of the dental tissue of the patient into a machine learning model, wherein the machine learning model has been trained as function of training data comprising sets of dental images correlated with sets of medical data; and
predicting, using the medical device, a medical condition for the patient as a function of the machine learning model and the dental data.

A12. The method of paragraph A11, wherein the dental tissue comprises one or more of dental hard tissue and dental soft tissue.

A13. The method of paragraph A11, wherein the dental images comprise at least a two-dimensional digital color image representing the at least a surface of the dental tissue.

A14. The method of paragraph A13, wherein the dental images additionally comprise at least a three-dimensional image representing the at least a surface of the dental tissue.

A15. The method of paragraph A11, wherein the medical data comprises one or more of radiological images, pathological test results, electronic health records, and ECG data.

A16. The method of paragraph A11, further comprising:
pre-processing, using the computing device, the dental images; and
inputting, using the computing device, the pre-processed dental data into the machine learning model; and
wherein predicting the medical condition for the patient as a function of the machine learning model and the pre-processed dental data.

A17. The method of paragraph A16, wherein pre-processing the dental images comprises inputting the dental images into a pre-processing machine learning model; and pre-processing the dental images as a function of the pre-processing machine learning model and the dental images.

A18. The method of paragraph A17, wherein the pre-processing machine learning model comprises one or more of a transformer-based machine learning model, a classifier, and a neural network.

A19. The method of paragraph A16, wherein the pre-processing machine learning model comprises a 3D reconstruction model; and
pre-processing the dental images further comprises:
inputting, into the 3D reconstruction model, at least a two-dimensional digital color image representing the at least a surface of the dental tissue; and
outputting, from the 3D reconstruction model, at least a three-dimensional image representing the at least a surface of the dental tissue as a function of the 3D reconstruction model and the at least a two-dimensional digital color image representing the at least a surface of the dental tissue.

A20. The method of paragraph A19, wherein the dental data further comprises location data associated with the relative location of the at least a two-dimensional digital color image; and
pre-processing the dental images further comprises:
inputting, into the 3D reconstruction model, the at least a two-dimensional digital color image representing the at least a surface of the dental tissue and the location data; and
outputting, from the 3D reconstruction model, at least a three-dimensional image representing the at least a surface of the dental tissue as a function of the 3D reconstruction model, the at least a two-dimensional digital color image representing the at least a surface of the dental tissue, and the location data.

What is claimed is:

1. A system for associating dental and medical data the system comprising:
a processor; and
a memory containing instructions that instruct the processor to:
receive dental data comprising a plurality of dental images representative of at least a surface of dental tissue of a patient;
receive medical data representative of a non-dental medical condition and associated with the patient from an electronic health record (EHR) from hospital;
generate training data as a function of a correlation between the plurality of dental images and the medical data representative of the non-dental medical condition;
input the training data into a machine learning algorithm; and
train a machine learning model to predict the non-dental medical condition using dental images, as a function of the training data and the machine learning algorithm.

2. The system of claim 1, wherein the dental tissue comprises one or more of dental hard tissue and dental soft tissue.

3. The system of claim 1, wherein the dental images comprise at least a two-dimensional digital color image representing the at least a surface of the dental tissue.

4. The system of claim 3, wherein the dental images additionally comprise at least a three-dimensional image representing the at least a surface of the dental tissue.

5. The system of claim 1, wherein the non-dental medical data comprises ECG data.

6. The system of claim 1, wherein the memory contains further instructions that instruct the processor to:
pre-process the dental images; and
wherein generating the training data is performed as a function of a correlation between the pre-processed dental images and the medical data.

7. The system of claim 6, wherein pre-processing the dental images comprising inputting the dental images into a pre-processing machine learning model; and
pre-processing the dental images as a function of the pre-processing machine learning model and the dental images.

8. The system of claim 7, wherein the pre-processing machine learning model comprises a transformer-based machine learning model.

9. The system of claim 6, wherein the pre-processing machine learning model comprises a 3D reconstruction model, wherein the 3D reconstruction model is context-aware; and
pre-processing the dental images further comprises:
inputting, into the 3D reconstruction model, at least a two-dimensional digital color image representing the at least a surface of the dental tissue; and
outputting, from the 3D reconstruction model, at least a three-dimensional image comprising a mesh image and representing the at least a surface of the dental tissue as a function of the 3D reconstruction model and the at least a two-dimensional digital color image representing the at least a surface of the dental tissue.

10. The system of claim 9, wherein the dental data further comprises location data associated with the relative location of the at least a two-dimensional digital color image; and
pre-processing the dental images further comprises:
inputting, into the 3D reconstruction model, the at least a two-dimensional digital color image representing the at least a surface of the dental tissue and the location data; and
outputting, from the 3D reconstruction model, at least a three-dimensional image representing the at least a surface of the dental tissue as a function of the 3D reconstruction model, the at least a two-dimensional digital color image representing the at least a surface of the dental tissue, and the location data.

11. A method of associating dental and medical data the method comprising:
receiving, using a computing device, dental data comprising a plurality of dental images representative of at least a surface of dental tissue of a patient;
receiving, using the computing device, medical data representative of a non-dental medical condition and associated with the patient from an electronic health record (EHR) from a hospital;
generating, using the computing device, training data as a function of a correlation between the plurality of dental images and the medical data representative of the non-dental medical condition;
inputting, using the computing device, the training data into a machine learning algorithm; and
training, using the computing device, a machine learning model to predict the non-dental medical condition using dental images, as a function of the training data and the machine learning algorithm.

12. The method of claim 11, wherein the dental tissue comprises one or more of dental hard tissue and dental soft tissue.

13. The method of claim 11, wherein the dental images comprise at least a two-dimensional digital color image representing the at least a surface of the dental tissue.

14. The method of claim 13, wherein the dental images additionally comprise at least a three-dimensional image representing the at least a surface of the dental tissue.

15. The method of claim 11, wherein the non-dental medical data comprises ECG data.

16. The method of claim 11, further comprising pre-processing, using the computing device, the dental images; and
   wherein generating the training data is performed as a function of a correlation between the pre-processed dental images and the medical data.

17. The method of claim 16, wherein pre-processing the dental images comprises inputting the dental images into a pre-processing machine learning model; and
   pre-processing the dental images as a function of the pre-processing machine learning model and the dental images.

18. The method of claim 17, wherein the pre-processing machine learning model comprises transformer-based machine learning model.

19. The method of claim 16, wherein the pre-processing machine learning model comprises a 3D reconstruction model; and
   pre-processing the dental images further comprises:
      inputting, into the 3D reconstruction model, at least a two-dimensional digital color image representing the at least a surface of the dental tissue, wherein the 3d reconstruction model is context-aware; and
      outputting, from the 3D reconstruction model, at least a three-dimensional image comprising a mesh image and representing the at least a surface of the dental tissue as a function of the 3D reconstruction model and the at least a two-dimensional digital color image representing the at least a surface of the dental tissue.

20. The method of claim 19, wherein the dental data further comprises location data associated with the relative location of the at least a two-dimensional digital color image; and
   pre-processing the dental images further comprises:
      inputting, into the 3D reconstruction model, the at least a two-dimensional digital color image representing the at least a surface of the dental tissue and the location data; and
      outputting, from the 3D reconstruction model, at least a three-dimensional image representing the at least a surface of the dental tissue as a function of the 3D reconstruction model, the at least a two-dimensional digital color image representing the at least a surface of the dental tissue, and the location data.

* * * * *